United States Patent
Liu et al.

(10) Patent No.: US 10,064,862 B2
(45) Date of Patent: Sep. 4, 2018

(54) ANTIVIRAL AXIN STABILIZER

(71) Applicant: The Board of Regents for Oklahoma State University, Stillwater, OK (US)

(72) Inventors: Lin Liu, Edmond, OK (US); Yujie Guo, Guangzhou (CN)

(73) Assignee: THE BOARD OF REGENTS FOR OKLAHOMA STATE UNIVERSITY, Stillwater, OK (US)

( * ) Notice: Subject to any disclaimer, the term of this patent is extended or adjusted under 35 U.S.C. 154(b) by 0 days.

(21) Appl. No.: 15/123,030

(22) PCT Filed: Mar. 3, 2015

(86) PCT No.: PCT/US2015/018524
§ 371 (c)(1),
(2) Date: Sep. 1, 2016

(87) PCT Pub. No.: WO2015/134525
PCT Pub. Date: Sep. 11, 2015

(65) Prior Publication Data
US 2017/0065587 A1 Mar. 9, 2017

Related U.S. Application Data

(60) Provisional application No. 61/947,766, filed on Mar. 4, 2014.

(51) Int. Cl.
*A61K 31/522* (2006.01)
*A61K 31/517* (2006.01)
*A61K 31/4709* (2006.01)
*A61K 31/352* (2006.01)
*A61K 31/4196* (2006.01)
*A61K 31/422* (2006.01)
*A61K 31/4375* (2006.01)
*A61K 31/473* (2006.01)
*A61K 31/4743* (2006.01)
*A61K 31/4365* (2006.01)
*A61K 9/00* (2006.01)

(52) U.S. Cl.
CPC .......... *A61K 31/517* (2013.01); *A61K 31/352* (2013.01); *A61K 31/4196* (2013.01); *A61K 31/422* (2013.01); *A61K 31/4365* (2013.01); *A61K 31/4375* (2013.01); *A61K 31/473* (2013.01); *A61K 31/4709* (2013.01); *A61K 31/4743* (2013.01); *A61K 9/0034* (2013.01); *A61K 31/522* (2013.01)

(58) Field of Classification Search
CPC .............................. A61K 31/522; A61K 9/0034
USPC ....................................................... 514/266.3
See application file for complete search history.

(56) References Cited

U.S. PATENT DOCUMENTS

2014/0255426 A1* 9/2014 Silvestri ............... A61K 31/167
424/160.1

FOREIGN PATENT DOCUMENTS

WO 2013/106934 A1 7/2013

OTHER PUBLICATIONS

Guo, Y., "Developmental Signaling and Acute Lung Injury (Doctoral Dissertation)", May 31, 2014, pp. 1-143, Publisher: Oklahoma State University, Published in: US.
Shapira et al., "A Physical and Regulatory Map of Host-Influenza Interactions Reveals Pathways in H1N1 Infection", Dec. 24, 2009, pp. 1255-1267, vol. 139, No. 7, Publisher: National Institutes of Health, Published in: US.
Optumrx, "Respiratory Syncytial Virus (RSV)," 2012, pp. 1-4, Retrieved from Internet Apr. 24, 2015.
PCT/US2015/018524, (The Board of Regents for Oklahoma State University), International Search Report and Written Opinion, dated May 20, 2015.

* cited by examiner

*Primary Examiner* — Kevin E Weddington
(74) *Attorney, Agent, or Firm* — Crowe & Dunlevy; Terry L. Watt

(57) ABSTRACT

Methods and compositions for preventing and/or treating viral infections are provided. The methods involve administering an agent that stabilizes or enhances Axin1 activity, e.g. and agent that inhibits tankyrase. Administration of the agent stimulates or increases interferon activity, thereby preventing or lessening at least one symptom of virus infection. The virus infection may be caused by a respiratory virus such as influenza virus.

18 Claims, 15 Drawing Sheets

Specification includes a Sequence Listing.

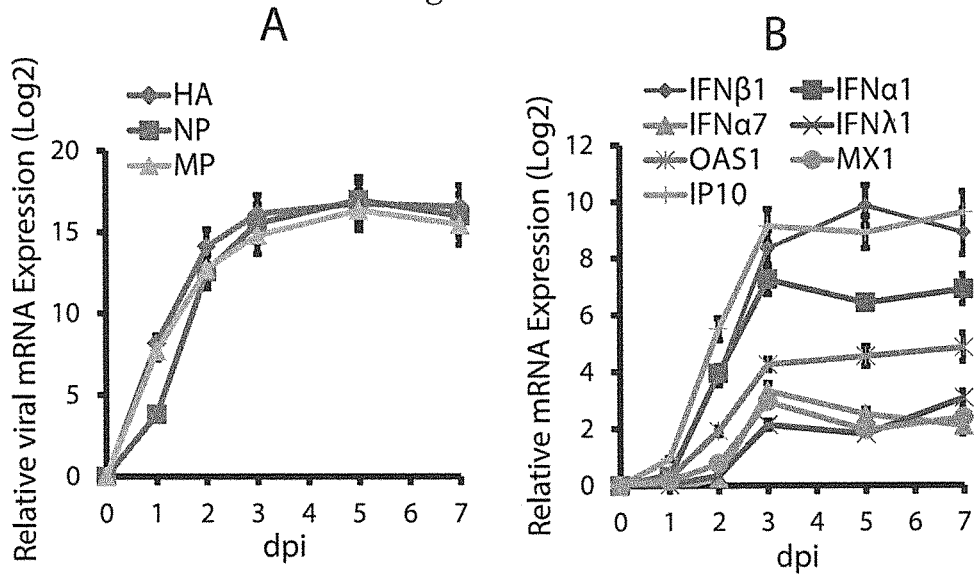
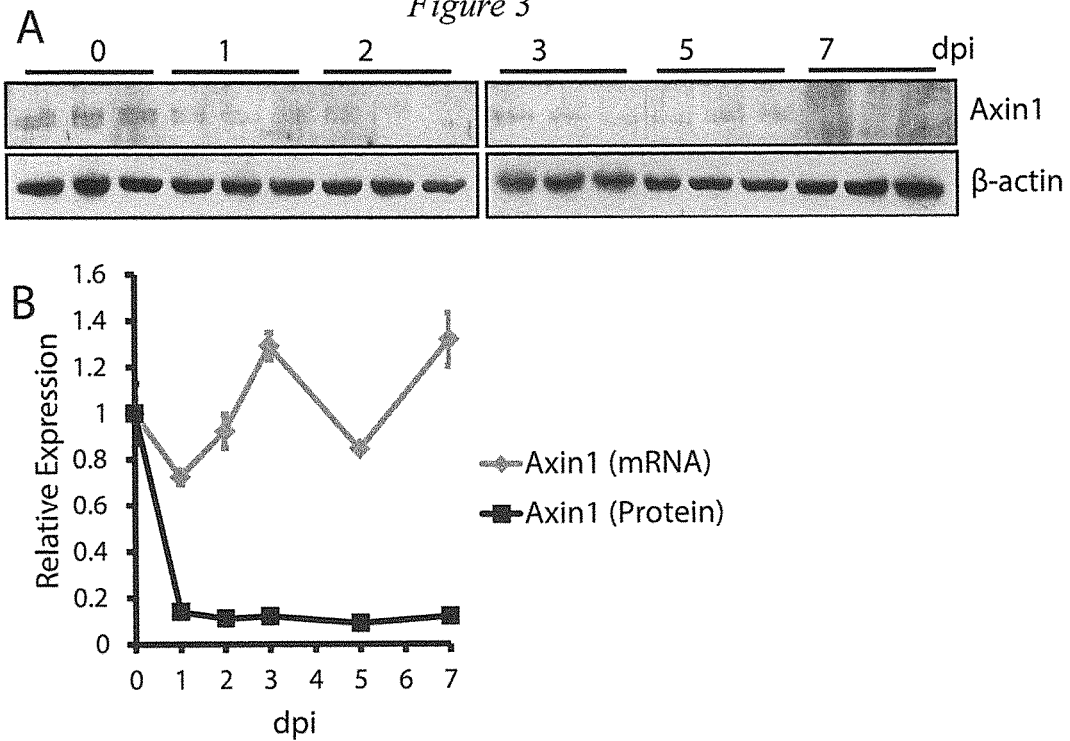

*Figure 17*
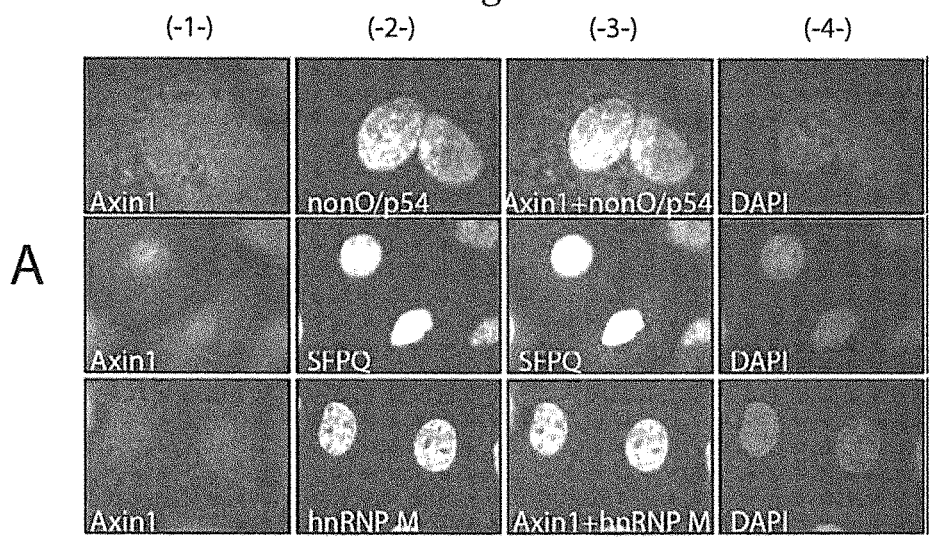
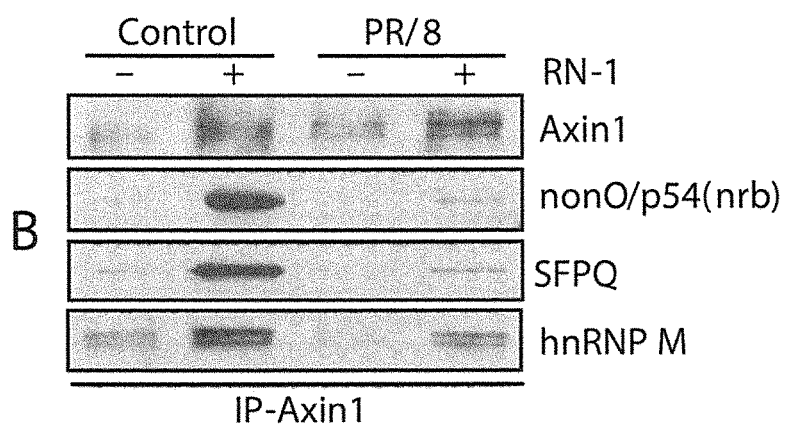

SEQUENCE LISTING

<160> NUMBER OF SEQ ID NOS: 42

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 1
attgctcaat ctcgggtggc tg                                          22

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 2
cgttcttagt tggtggagcg atttg                                       25

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 3
ctccaagcag aggacaaaat ca                                          22

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 4
ggatgggttc cccacagaaa ta                                          22

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 5
cagctccaag aaaggacgaa c                                           21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 6
ggcagtgtaa ctcttctgca t                                           21

<210> SEQ ID NO 7
<211> LENGTH: 18
<212> TYPE: DNA
<213> ORGANISM: Artificial Sequence

```
<220> FEATURE:
<223> OTHER INFORMATION: Synthetic oligonucleotide primer

<400> SEQUENCE: 7
tctgatgcag caggtggg                                                   18

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 8
agggctctcc agacttctgc tctg                                            24

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 9
tgatgagcta ctactggtca gc                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 10
gatctcttag cacaaggatg gc                                              22

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 11
atgaacgcta cacactgcat c                                               21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 12
ccatcctttt gccagttcct c                                               21

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 13
ctttgatgtc ctgggtcatg t                                               21
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
gctccgtgaa gcaggtagag                                                    20

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 15
gaaggcaagg tcttggatg                                                     19

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 16
gctgacctct gcacttgact                                                    20

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 17
ccaagtgctg ccgtcatttt c                                                  21

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 18
ggctcgcagg gatgatttca a                                                  21

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 19
gtaacccgtt gaaccccatt                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide primer
```

<400> SEQUENCE: 20
ccatccaatc ggtagtagcg                                                    20

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 21
catgtacgtt gctatccagg c                                                  21

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 22
ctccttaatg tcacgcacga t                                                  21

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 23
atgaccaaca agtgtctcct cc                                                 22

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 24
ggaatccaag caagttgtag ctc                                                23

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 25
gcctcgccct ttgctttact                                                    20

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 26
ctgtgggtct cagggagatc a                                                  21

<210> SEQ ID NO 27

```
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 27
agggccttga tactcctgg                                                  19

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 28
tcctcctccg ggaatctgaa t                                               21

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 29
tcggtaactg acttgaatgt cca                                             23

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 30
tcgcttccct gttttagctg c                                               21

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 31
tgtccaaggt ggtaaagggt g                                               21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 32
ccggcgattt aactgatcct g                                               21

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 33
```

```
gtttccgaag tggacatcgc a                                              21

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 34
ctgcacaggt tgttctcagc                                                20

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 35
gtggcattca aggagtacct c                                              21

<210> SEQ ID NO 36
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 36
tgatggcctt cgattctgga tt                                             22

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 37
ggcccaacca caacacaaac                                                20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 38
agccctcctt ctccgtcagc                                                20

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 39
tgtgtatgga cctgccgtag c                                              21

<210> SEQ ID NO 40
<211> LENGTH: 23
<212> TYPE: DNA
```

```
<213> ORGANISM: Artificial Sequence
<220> FEATURE:
<223> OTHER INFORMATION: Synthetic oligonucleotide primer

<400> SEQUENCE: 40
ccatccacac cagttgactc ttg                                          23

<210> SEQ ID NO 41
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 41
cttctaaccg aggtcgaaac gta                                          23

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 42
ggtgacagga ttggtcttgt cttta                                        25
```

ANTIVIRAL AXIN STABILIZER

CROSS REFERENCE TO RELATED APPLICATIONS

This application claims the benefit of U.S. Provisional Patent Application Ser. No. 61/947,766 filed on Mar. 4, 2014, and incorporates said provisional application by reference into this document as if fully set out at this point.

SEQUENCE LISTING

This application includes as the Sequence Listing the complete contents of the accompanying text file "Sequence.txt", created Mar. 3, 2015, containing 4,096 bytes, hereby incorporated by reference.

TECHNICAL FIELD

The present invention relates to the field of antiviral therapies in general and, more specifically, to antiviral therapies where interferon responses are provoked.

BACKGROUND

The influenza virus belongs to the Orthomyxoviridae family and is classified into three types: A, B and C according to their internal protein sequences. With the global pandemic potential and up to 500,000 annual deaths worldwide during seasonal epidemics, influenza A virus is a major public health concern and causes enormous economic burden. Prevention relying on vaccination has several limitations, including the lag time for vaccine manufacture and the low coverage rate. Considering the increasing level of viral resistance to current anti-influenza drugs targeting neuraminidase (NA) or M2 channel, it is particularly important to develop novel antiviral medicine.

Interferon (IFN) was discovered in 1957 as an agent that can inhibit (interfere with) the replication of influenza virus. The IFN family of cytokines is now recognized as the most potent vertebrate-derived signals for mobilizing antimicrobial effector functions against intracellular pathogens. Three classes of IFN has been identified and classified according to the receptor complex they signal through: Type I interferons (IFNβ, 14 IFNαs, IFδ, IFNε, IFNκ, IFNo and IFNτ), best known for their antiviral properties, mediate the induction of both the innate immune response and subsequent adaptive immunity to viruses; Type II interferon (IFNγ) stimulates broad immune response to various pathogens other than viruses; and, Type III interferons (3 IFNλs) are also known to regulate antiviral response and are proposed as ancestral type I IFN. It is widely accepted that viral attachment and viral dsRNA intermediates accumulating during virus replication are the primary mediators triggering IFNs production, which ultimately results in expression of thousands of IFN-stimulated genes (ISGs) (OAS1, MX1, etc.) and limits virus replication.

In the early phase of infection, Toll-like receptors, cytosolic RIG-1-like receptors (RIG-1 and MDA5), NOD-like receptors and C-type lectin receptors are major players involved in innate recognition of influenza virus. Recently, the novel IFN-regulated viral RNA sensor interferon-induced protein with tetratricopeptide repeats 1 (IFIT1) was identified as having antiviral properties. Activation of type I IFN expression by these pattern recognition receptors (PRRs) is highly controlled by several transcription factors (TFs) including c-Jun/ATF2 (AP1), interferon regulatory factor 3/7 (IRF3/7), and p50/p65 (NF-κB). Smad3, as a transcription factor, also enhances type I IFN expression by cooperating with IRF7. In the later phase of infection, secreted type I IFN signal stimulates type I IFN receptor (IFNAR1/2) in an autocrine and paracrine fashion, which leads to the activation of Janus kinase (JAK)—signal transducer and activator of transcription (STAT) pathway, and finally turns on cellular antiviral status.

Axin, which was identified from analysis of the mouse-Fused locus, is a negative regulator of Axis formation in the development of mouse embryos. Axin protein, present in two isoforms (Axin1 and Axin2), acts as an architectural platform for the degradation of the oncogenic protein β-catenin. Axin1 has, in fact, emerged as a multidomain scaffolding protein for many other signaling pathways, including c-Jun-NH$_2$-kinase (JNK) mitogen-activated protein kinase (MAPK) signaling, p53 signaling, and transforming growth factor β (TGF-β) signaling. Axin1 forms a complex with MEKK1/4 and mediates JNK/c-Jun activation through MKK4/7. Axin1 also promotes Smad3 phosphorylation in response to TGF-β, and down-regulates the negative factor, Smad7, in TGF-β signaling. By forming a ternary complex, Axin1 stimulates p53 functions via activation of homeodomain-interacting protein kinase-2 (HIPK2) kinase. These intriguing β-catenin-independent roles of Axin1 open the door to its function in multiple physiological and pathological processes. With respect to infectious diseases, Axin1 apparently displays a preventive effect on bacterial *Salmonella* invasiveness and modulates inflammatory responses during infection. On the other hand, silencing of Axin1 up-regulates human immunodeficiency virus type I (HIV-1) gene expression and viral replication. Recently, XAV939, termed RN-1 in this study, was discovered to specifically inhibit poly(ADP-ribose) polymerase tankyrase1/2 (TNK1/2), which induces poly(ADP-ribosyl)ation (PARylation) of Axin1 and in turn promotes its proteasome-mediated degradation.

Before proceeding to a description of the present invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

Acute respiratory infection by influenza virus is a persistent and pervasive public health problem. Antiviral innate immunity initiated by type I interferon (IFN) is the first responder to pathogen invasion and provides the first line of defense. Using the influenza virus as an example of viral infection, described herein is the discovery that the scaffold protein Axin1 boosts the type I IFN response to influenza virus infection, thereby attenuating symptoms of viral infection. Without being bound by theory, it appears that this occurs in part through the stimulation, by Axin 1, of JNK/c-Jun and Smad3 signaling. It is also shown herein that Axin1 cooperates with interferon-induced protein with tetratricopeptide repeats 1 (IFIT1), a viral RNA sensor, to amplify the synthesis of type I IFN and to fine-tune the system of virus sensing. In addition, Axin1 specifically promoted the degradation of hnRNP M, a nucleoprotein required for efficient activity of influenza virus polymerases. Thus, in mammals, Axin1 plays a major role in mounting a successful immune response to infection by influenza virus.

Unfortunately, if left unchecked, influenza virus infection causes the degradation of Axin1, thereby preventing a robust immune response in infected individuals. However, as shown in the Examples section herein, administration of a chemical stabilizer of Axin1 to a subject exposed to influenza virus advantageously prevents Axin1 degradation, reduces influenza virus replication and protects from influenza virus infection. Thus, based on these new mechanistic insights into the regulation of type I IFN response by Axin1, this disclosure provides new methods and compositions for stabilizing, preserving or augmenting Axin1 activity in order to prevent or treat symptoms of infection by viruses, including the exemplary influenza virus. For example, the Axin1 stabilizer XAV939 is provided as a broad-spectrum antiviral agent.

Other embodiments and variations are certainly possible within the scope of the instant invention and can readily be formulated by those of ordinary skill in the art based on the disclosure herein.

The foregoing has outlined in broad terms the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

FIGS. 2A and B. Virus replication and IFN response in influenza virus infected mouse lungs. Mice were challenged with H1N1 influenza A/PR/8/34 virus (250 pfu/mouse) intranasally and the lungs were collected at 1 to 7 dpi. Relative mRNA expressions of (A) viral genes (HA, NP, and MP), (B) type I IFN (IFNβ1, IFNα1, and IFNα7), type III IFN (IFNλ1), and ISGs (OAS1, MX1, and IP10) in whole lung tissues were measured by Real-time PCR and normalized to 18S rRNA. Results were expressed as Log 2 (Value) and represented as means±s.e.m., n=3.

FIGS. 3 A and B. Axin1 is degraded during influenza pneumonia. Mice were intranasally infected with H1N1 influenza A/PR/8/34 virus (250 pfu/mouse) and the lungs were isolated at 1 to 7 dpi. (A) Axin1 protein level in harvested lung tissues were measured by Western blot using β-actin as an internal control. (B) Relative band intensity of Axin1 was quantified and normalized to β-actin. mRNA expression of Axin1 in the same lung tissues were measured by Real-time PCR and normalized to 18S rRNA. Both results (protein and mRNA) were expressed as a ratio to control (0 dpi). Data shown are means±s.e.m., n=3.

FIGS. 17A and B. Interactions between Axin1 and NonO/p54, SFPQ, and hnRNP M are lost during influenza virus replication. (A) Double immunostaining of Axin1 (-1-) and NonO/p54, SFPQ, and hnRNP M (-2- and -3-) with DAPI nuclear staining (-4-). Scale bar=10 μm. (B) A549 cells were pretreated with 20 μM RN-1 or 0.05% DMSO for 24 hours. Cells were then infected with H1N1 influenza A/PR/8/34 virus (MOI=2) for 24 hours. Axin1 was pulled down from lysed cells by immunoprecipitation and probed with indicated antibodies by Western blot.

DETAILED DESCRIPTION

Figure 1:
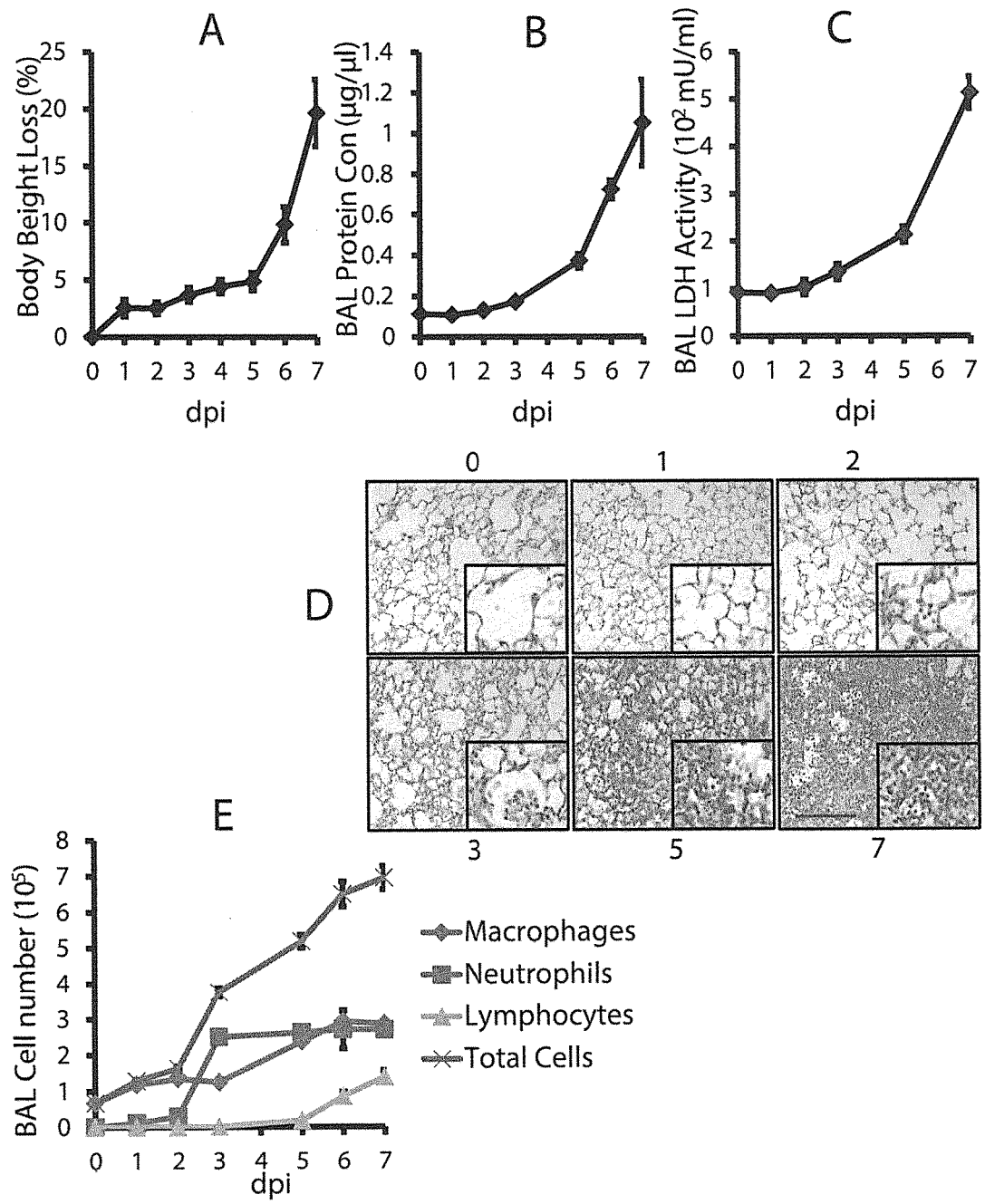
FIG. 1A-E. Acute lung inflammation and injury in influenza virus-infected mouse lungs. Mice were intranasally inoculated with H1N1 influenza A/PR/8/34 virus (250 pfu/mouse). The lung tissue and BALs were collected at 1 to 7 days post infection (dpi). (A) Body weight. (B) BAL protein concentration and (C) BAL LDH activity. (D) H&E staining of paraffin sections of lungs. Scale bar=100 μm. (E) Differential immune cells number in BAL. Values were shown as means±s.e.m., n=3.

The present disclosure is directed to compositions and methods for treating viral infections. In an exemplary embodiment, a tankyrase inhibitor is utilized therapeutically to enhance a type I interferon response. The disclosed methods of treating and/or preventing infection are useful for any type of viral infection or challenge that provokes an interferon response. Respiratory viruses particularly may fall within this domain, including exemplary influenza virus infections.

By way of introduction, the instant inventors searched for novel host factors functioning in influenza virus replication and IFN responses during viral infection, and explored new antivirals based on identified targets. It was first discovered that Axin1 was degraded in a mouse model of influenza virus-associated pneumonia. It was then demonstrated that Axin1 boosted IFN responses and inhibited influenza virus replication through the activation of JNK/c-Jun pathway and Smad3 signaling. The physical interaction between Axin1 and the viral RNA sensor IFIT1 was also detected. In addition, it was found that Axin1 specifically associated with another host protein, hnRNP M, which is required for virus replication and promoted its degradation. XAV939, an Axin stabilizer, attenuated symptoms or influenza viral pneumonia and protected animals from lethal influenza virus challenge. The instant inventors have, for the first time, recruited Axin1, the 15-years old scaffold protein, into the antiviral network of interferon.

Accordingly, provided herein are compositions and methods of using the compositions to prevent and/or treat symptoms of viral infection. Any type of viral infection or challenge that provokes an interferon response may be prevented/and or treated using the compositions disclosed herein. In one aspect, the viral infection that is prevented/treated is a respiratory viral infection. Examples of respiratory viruses include but are not limited to: influenza virus, respiratory syncytial virus, rhinoviruses, coronaviruses, parainfluenza viruses, adenoviruses, enteroviruses, measles, herpesviruses, reoviruses, human metapneumoviruses, SARS-coronaviruses, Epstein-Barr viruses, cytomegalovirus, hantaviruses, bocavirus, etc. In other aspects, the infection that is prevented/treated is caused by a virus that is not a respiratory virus, examples of which include but are not limited to Ebola virus, human immunodeficiency virus, hepatitis viruses, rotaviruses, Dengue virus, human papillomaviruses, BK polyomavirus, human parvovirus, human, T-lymphotropic virus, Rabies virus, West Nile virus, Yellow fever virus, smallpox, human bocavinus, parvovirus, human astrovirus, Norwalk virus, coxsackievirus, poliovirus, rubella virus, guanarito virus, junin virus, lassa virus, machupo virus, sabia virus, Crimean-Congo hemorrhagic fever virus, Marburg virus, Mumps virus, Hendra virus, Nipah virus, rotavirus, orbivirus, coltivirus, Banna virus, etc.

In one aspect, the virus is an influenza virus, and may be type A, B or C. If the virus is influenza A, any subtype may be prevented or treated, e.g. subtypes H1 through H18 and N1 through N11 respectively, such as H1N1 (including "2009 H1N1") and H3N2 viruses. If the virus is influenza B, any lineage may be prevented or treated, including B/Yamagata and B/Victoria.

In one aspect, the present invention provides compositions for use in eliciting an immune response (especially an interferon response) and/or vaccinating an individual against infection by a virus. The compositions include one or more substantially purified stabilizers or enhancers of Axin1 activity e.g. agents that increase or maintain Axin1 activity, and a pharmacologically suitable carrier. Exemplary agents include inhibitors of factors which degrade or otherwise inhibit Axin1 activity. Examples of such inhibitors include but are not limited to: tankyrase inhibitors, ubiquitination (E3 ligase, Smurf2) inhibitors, SUMOylation inhibitors, phosphatase (PP2A and PP2C) inhibitors. Exemplary tankyrase inhibitors include but are not limited to various small molecule inhibitors, various macromolecule inhibitors and various recombinant peptide inhibitors.

In some aspects, the agent is a small molecule inhibitor of tankyrase such as, for example: WIKI4 (2-[3-[[4-(4-Methoxyphenyl)-5-(4-pyridinyl)-4H-1,2,4-triazol-3-yl]thio]propyl]-1H-benz[de]isoquinoline-1,3(2H)-dione); XAV939 (3,5,7,8-Tetrahydro-2-[4-(trifluoromethyl)phenyl]-4H-thiopyrano[4,3-d]pyrimidin-4-one); TNKSi49 (N-((1r,4r)-4-(4-cyanophenoxy)cyclohexyl)-3-((4-oxo-3,4-dihydroquinazolin-2-yl)thio)propanamide); IWR-1 (4-(1,3,3a,4,7,7a-Hexahydro-1,3-dioxo-4,7-methano-2H-isoindol-2-yl)-N-8-quinolinyl-Benzamide); G007-LK (4-(5-((E)-2-(4-(2-Chlorophenyl)-5-(5-(methylsulfonyl)pyridin-2-yl)-4H-1,2,4-triazol-3-yl)ethenyl)-1,3,4-oxadiazol-2-yl)benzonitrile); JW55 (N-(4-(((4-(4-methoxyphenyl)tetrahydro-2H-pyran-4-yl)methyl)carbamoyl)phenyl)furan-2-carboxamide); JW74 (5-(((4-(4-methoxyphenyl)-5-(pyridin-4-yl)-4H-1,2,4-triazol-3-yl)thio)methyl)-3-(p-tolyl)-1,2,4-oxadiazole); TNKS1/2 Inhibitor III (3-(4-Methoxyphenyl)-5-((4-(4-methoxyphenyl)-5-methyl-4H-1,2,4-triazol-3-ylthio)methyl)-1,2,4-oxadiazole), Tankyrase Inhibitors (TNKS) 22 (3-((4-oxo-3,4-dihydroquinazolin-2-yl)thio)-N-((1r,4r)-4-(5-phenyl-1,3,4-oxadiazol-2-yl)cyclohexyl)propanamide);

1,2,-Trizole;

flavone (2-phenyl-4H-chromen-4-one)

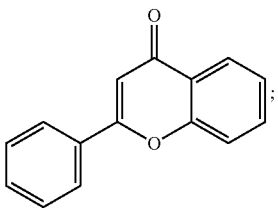 [SMILES: O=c1cc(-c2ccccc2)oc2ccccc12]

phenanthridin-6(5H)-one

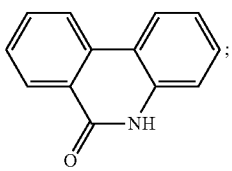 [SMILES: O=c1[nH]c2ccccc2c2ccccc12]

TIQ-A

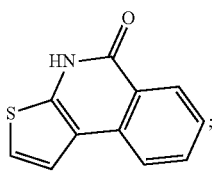 [SMILES: O=c1[nH]c2sccc2c2ccccc12]

PJ34

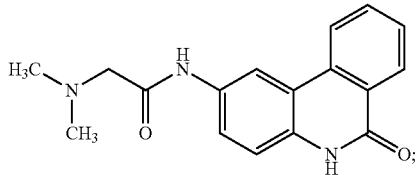 [SMILES: CN(C)CC(=O)Nc1ccc2[nH]c(=O)c3ccccc3c2c1]

1DY(N-(2-methoxyphenyl)-4-{[3-(4-oxo-3,4-dihydro-quinazolin-2-yl) propanoyl]amino}benzamide)

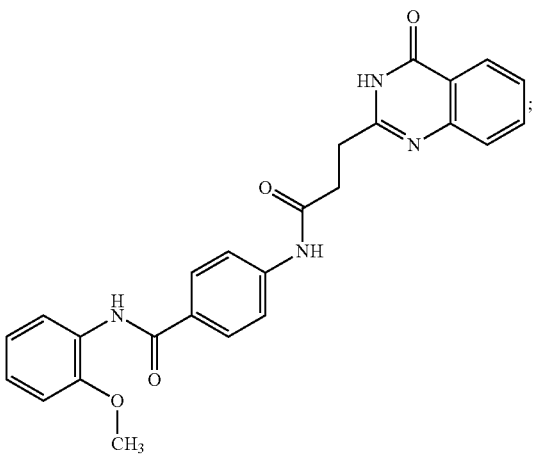 [SMILES: COc1ccccc1NC(=O)c1ccc(NC(=O)CCc2nc3ccccc3c(=O)[nH]2)cc1]

oxazolidinone

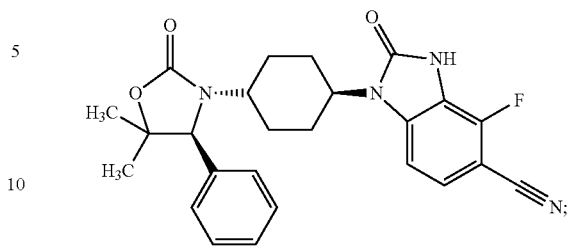

etc.

The small molecule inhibitor may be XAV-939 and various active forms thereof; such as a prodrug of XAV-939, an active metabolite of XAV-939 or a salt of XAV-939. Combinations of these are also contemplated. Active derivatives or variants of these molecules may also be employed, so long as the derivative or variant displays at least 50% of the tankyrase inhibitory activity of the parent molecule from which it is derived, and usually at least about 60, 70, 80, 90, or 100% or more of the activity of the parent. The derivative or variant may be more active than the parent molecule.

In other aspects, the agent is a macromolecule inhibitor such as a protein or RNA that has ability to inhibit tankyrase activity.

In other aspects, the agent is a recombinant peptide inhibitor that is composed of short chains of individual amino acids linked by amide bonds and has ability to inhibit tankyrase activity.

The preparation of therapeutic compositions is generally known to those of skill in the art. Typically, such compositions are prepared either as liquid solutions or suspensions, however solid forms such as tablets, pills, powders and the like are also contemplated. The liquid may be aqueous or oil-based suspensions or solutions. Solid forms suitable for solution in, or suspension in, liquids prior to administration may also be prepared. The preparation may also be emulsified. The active ingredients may be mixed with excipients which are pharmaceutically acceptable and compatible with the active ingredients, e.g. pharmaceutically acceptable salts. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of active agent(s) in the formulations may vary. However, in general, the amount in the formulations will be from about 1-99%. Still other suitable formulations for use in the present invention can be found, for example in Remington's Pharmaceutical Sciences, Philadelphia, Pa., 19th ed. (1995).

Some examples of materials which can serve as pharmaceutically acceptable carriers include, but are not limited to, ion exchangers, alumina, aluminum stearate, lecithin, serum proteins (such as human serum albumin), buffer substances (such as TWEEN® 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compositions may be administered in vivo by any suitable route including but not limited to: inoculation or injection (e.g. intravenous, intraperitoneal, intramuscular, subcutaneous, and the like), and by absorption through epithelial or mucocutaneous linings (e.g., nasal, oral, and the like). Other suitable means include but are not limited to: inhalation (e.g. as a mist or spray), orally (e.g. as a pill, capsule, liquid, etc.), intranasally, as eye drops, etc. In preferred embodiments, the mode of administration is oral or by injection. In addition, the compositions may be administered in conjunction with other treatment modalities such as substances that boost the immune system, antibiotic agents, and the like.

The methods of this disclosure involve administering an active agent to a subject in need or protection from or treatment of a viral infection. Such methods typically involve identifying a suitable subject e.g. an individual who has been or is likely to be exposed to an infectious virus, and administering a therapeutically effective dose of the active agent to the subject. In some aspects, what is provided is a method of prophylactically preventing the establishment of a virus infection in an individual, e.g. preventing or lessening the development of at least one symptom of a viral infection (e.g. fever or feeling feverish/chills, cough, sore throat, runny or stuffy nose, muscle or body aches, headaches, fatigue (tiredness), vomiting and diarrhea (more common in children than adults). Secondary effects or complications of virus infection are also prevented, including weight loss, pneumonia, bronchitis, sinus and ear infections and worsening of chronic health problems such as asthma, chronic congestive heart failure, etc.

The dose of active agent and the timing and mode of administration varies from individual to individual e.g. based on the type of virus; the stage of infection (if an infection is already present); the age, gender, genetic background, and overall general health of the individual, etc., and is best determined by a skilled medical practitioner such as a physician. Generally, the dose will be in the range of from about 1 to about 500 mg/kg of body weight. Frequency of administration generally ranges from 1 to 4 times per day, although slow release formulations may permit administration daily or every few days.

In some aspects, the compositions described herein are administered as a preventative measure (prophylactically), e.g. they are administered before disease symptoms appear. In such aspects, subjects in need of such preventative treatment are generally those that are at risk of developing a disease caused by a virus. The risk may be due to a known past exposure to an infectious virus, or due to a likely or possible future exposure that is anticipated e.g. based on past patterns of outbreaks and epidemics. In some aspects, the invention provides methods of protecting a subject against diseases caused by viruses. In other words, the subject to whom the agent is administered does not experience one or more symptoms of the disease that would occur, if the agent was not administered. In some aspects, all disease symptoms may be entirely avoided. However, those of skill in the art will recognize that much benefit may accrue if one or more symptoms are only lessened or attenuated, but are not completely prevented. In other aspects, the subject to whom the agent is administered already has one or more symptoms of a disease such as a virus infection. In this case, the present compositions and methods are used to treat the disease. Accordingly, one or more established disease symptoms is eradicated, or at least lessened, or the duration is of the disease is shortened, compared to what would have occurred in the absence of administration.

In some aspects, what is provided is a method of increasing, provoking stimulating, etc. an interferon (IFN) response in a subject in need thereof. This method comprises administering to the subject a therapeutically effective amount of one or more Axin1 stabilizers or enhancers, as described herein. The interferon response generally is evidenced by an increase in the level and/or activity of one or more of IFN I, IFN II and IFN III. Generally, the level and/or activity of IFN I is elevated.

EXAMPLES

Materials and Methods

Animals:

All male C57BL/6N mice (6-8 weeks old) were obtained from Jackson Laboratory (Bar Harbor, Me.), housed and cared for by the Laboratory Animal Resource Unit operated by the Center for Veterinary Health Sciences, Oklahoma State University. Experimental protocols were reviewed and approved by the Institutional Animal Care and Use Committee of Oklahoma State University.

Influenza Virus:

Influenza virus H1N1 strain A/Puerto Rico/8/1934 was obtained from American Type Culture Collection (ATCC, Manassas, Va.) and stored at −80° C.

Mouse Model of Influenza Viral Pneumonia:

Male C57BL/6N mice (6-8 weeks of age) were anesthetized by intraperitoneal injection of ketamine (80 mg/kg body weight) and xylazine (10 mg/kg body weight), and inoculated with influenza virus A/Puerto Rico/8/1934 H1N1 (250 pfu/mouse) intranasally. Mice were weighed daily for the evaluation of loss of body weights and clinical signs such as ruffled fur and respiratory distress. Animals were sacrificed on days 0-7 post infection. Unlavaged lungs were homogenized in liquid nitrogen by mortar and pestle, aliquoted and stored at −80° C. for further use.

BAL Analysis:

Lungs were lavaged with 1 ml of normal saline three times. Bronchoalveolar lavages (BAL) were centrifuged at 380 g for 10 min at 4° C. and the supernatants were stored at −80° C. for further analysis. Protein concentrations in BAL were measured by a Bio-Rad protein assay (Bio-Rad Laboratories, Hercules, Calif.). Lactate dehydrogenase (LDH) activity in BAL was determined by a Cytotoxicity Detection kit (Roche Applied Sciences, Indianapolis, Ind.) with type III L-lactic dehydrogenase (SIGMA, St. Louis, Mo.) as standards. BAL cells were resuspended in normal saline and total cells were counted using a hemocytometer. For differential cell counts, cytospinned cells on glass slides were stained with Wright-Giemsa.

Histopathology:

Unlavaged lungs were instilled with 4% paraformaldehyde in PBS at 20 cm $H_2O$ pressure and fixed for 72 hours, embedded in paraffin and sectioned at 4 µm thickness. The sections were stained with hematoxylin and eosin and were examined under a light microscope.

Survival Study of Lethal Dose Influenza Virus Infection:

Male C57BL/6N mice (6-8 week old) were challenged intranasally with a lethal dose (1,000 pfu) of influenza virus A/PR/8/34 H1N1 under anesthesia. RN-1 (SIGMA, St. Louis, Mo.) was dissolved in dimethyl sulfoxide (DMSO) and given to the mice orally using metal oral gavage in a dose of 50 mg/kg mixed with 1% methylcellulose (50 µl/mouse) every day, beginning one day before infection (−1 dpi) and continuing until 2 or 4 days post infection. Control animals were given vehicle alone in the same formulation. All animals were observed daily for body weight loss and clinical signs of disease such as ruffled fur, inactivity and difficulty in breathing until 21 days post infection.

Cell Culture:

Human embryonic kidney 293 (HEK293), human lung epithelial A549 cells, and Madin-Darby canine kidney (MDCK) cells (ATCC, Manassas, Va.) were maintained in Earle's Minimal Essential Medium (EMEM) complemented with 10% fetal bovine serum (FBS). Human epithelial type 2 (HEp2) cells (ATCC, Manassas, Va.) were maintained in EMEM complemented with 10% FBS, Glutamine, and Non-Essential Amino Acids. E10 cells were cultured in CMRL1066 supplemented with 10% FBS and Glutamine. Cells were grown at 37° C. in a humidified atmosphere containing 5% $CO_2$.

Primary Mouse Alveolar Epithelial Type II Cells (AEC II) Isolation:

Murine AEC II cells were isolated from Male C57BL/6N mice (6-8 weeks of age) Briefly, lungs were perfused with solution II (0.9% NaCl, 0.1% glucose, 10 mM HEPES, 1.3 mM $MgSO_4$, 5 mM KCl, 1.7 mM $CaCl_2$, 0.1 mg/ml streptomycin sulfate, 0.06 mg/ml penicillin G, 3 mM $Na_2HPO4$ and 3 mM $NaH_2PO_4$, pH 7.4) to clear the blood. AEC II were released from the lung by digestion with dispase (250 caseinolytic units/ml, BD Biosciences, Franklin Lakes, N.J.). Then, the lung was chopped with a Mcliwain tissue chopper, and the lung slices were further digested with DNase I (100 µg/ml) for 45 min at 37° C. with intermittent shaking. The digested lung slices were then filtered through 160-, 37- and 15-µm nylon mesh sequentially. The filtrate was centrifuged at 250 g for 10 min at 4° C. The cell pellet was resuspended in Dulbecco's Modified Eagle's Medium (DMEM) supplemented with 10% FBS and incubated in a 100 mm Petri dish coated with mouse IgG (75 µg/dish) for 1 hour. The unattached cells were spun down at 250 g for 10 min at 4° C. and resuspended in DMEM containing 10% FBS. The isolated AEC II had a purity of 90% as determined by SP-C staining and a viability of over 98% as assessed by trypan blue exclusion. AEC II were cultured in 12-well tissue culture plates at $1 \times 10^6$ cells/well in DMEM containing 10% FBS, penicillin and streptomycin for 5 days before the use.

Plasmids and Transfection:

pCS2-based OE-GFP (15681), OE-Axin1 (21287) and OE-Axin2 (21279) plasmids were obtained from Addgene (Cambridge, Mass.). All three plasmid have myc-tag. TOP-Flash and FOPflash reporter plasmids were purchased from EMD Millipore (Billerica, Mass.). Smad3 signaling and ISRE-luc reporter plasmid was purchased from QIAGEN (Valencia, Calif.). pRL-TK Renilla luciferase plasmid was obtained from Progema (Madison, Wis.). HEK293 cells were cultured on 96-well tissue culture plates (dual luciferase assay) and 12-well tissue culture plates (all other experiments) until 90% confluence and then transfected with proper plasmids using Lipofectamine 2000 (Invitrogen, Carlsbad, Calif.).

In Vitro Influenza Virus Infection

HEK293, A549 and primary mouse AEC II cells were washed with serum-free complete DMEM and infected with influenza virus at the multiplicity of infection (MOI) of 2 in serum-free complete DMEM supplemented with 1 µg/ml L-1-tosylamide-2-phenylethyl chloromethyl ketone (TPCK)-treated trypsin (SIGMA, St. Louis, Mo.) for 1 hour. Then cells were changed into fresh serum-free complete medium and continually cultured for 2 to 48 hours.

Quantitative Real-time PCR:

Total RNA was extracted from cells or lung tissues using TRI-Reagent (Molecular Research Center, Cincinnati, Ohio) and digested with TURBO DNase (Ambion, Austin, Tex., USA) to remove the genomic DNA contamination. One μg of RNA was reverse-transcribed into cDNA using Moloney murine leukemia virus (M-MLV) reverse transcriptase (Invitrogen, Carlsbad, Calif.), random primers, and oligo dT (Promega, Madison, Wis.). Real-time PCR was carried out on 7900HT Fast Real-Time PCR System using SYBR Green I detection Master Mix (Eurogentec, Calif.) as described previously. The primers were designed using Primer Express® software (Applied Biosystems, Foster City, Calif.), and listed in Table 1.

TABLE 1

PCR primer sequences

| Gene | Species | Forward primers | Reverse primers |
| --- | --- | --- | --- |
| 18S | Mouse | ATTGCTCAATCTCGGGTGGCTG (SEQ ID NO: 1) | CGTTCTTAGTTGGTGGAGCGATTTG (SEQ ID NO: 2) |
| Axin1 | Mouse | CTCCAAGCAGAGGACAAAATCA (SEQ ID NO: 3) | GGATGGGTTCCCCACAGAAATA (SEQ ID NO: 4) |
| IFNβ1 | Mouse | CAGCTCCAAGAAAGGACGAAC (SEQ ID NO: 5) | GGCAGTGTAACTCTTCTGCAT (SEQ ID NO: 6) |
| IFNα1 | Mouse | TCTGATGCAGCAGGTGGG (SEQ ID NO: 7) | AGGGCTCTCCAGACTTCTGCTCTG (SEQ ID NO: 8) |
| IFNα7 | Mouse | TGATGAGCTACTACTGGTCAGC (SEQ ID NO: 9) | GATCTCTTAGCACAAGGATGGC (SEQ ID NO: 10) |
| IFNλ1 | Mouse | ATGAACGCTACACACTGCATC (SEQ ID NO: 11) | CCATCCTTTTGCCAGTTCCTC (SEQ ID NO: 12) |
| OAS1 | Mouse | CTTTGATGTCCTGGGTCATGT (SEQ ID NO: 13) | GCTCCGTGAAGCAGGTAGAG (SEQ ID NO: 14) |
| MX1 | Mouse | GAAGGCAAGGTCTTGGATG (SEQ ID NO: 15) | GCTGACCTCTGCACTTGACT (SEQ ID NO: 16) |
| IP10 | Mouse | CCAAGTGCTGCCGTCATTTTC (SEQ ID NO: 17) | GGCTCGCAGGGATGATTTCAA (SEQ ID NO: 18) |
| 18S | Human | GTAACCCGTTGAACCCCATT (SEQ ID NO: 19) | CCATCCAATCGGTAGTAGCG (SEQ ID NO: 20) |
| β-actin | Human | CATGTACGTTGCTATCCAGGC (SEQ ID NO: 21) | CTCCTTAATGTCACGCACGAT (SEQ ID NO: 22) |
| IFNβ1 | Human | ATGACCAACAAGTGTCTCCTCC (SEQ ID NO: 23) | GGAATCCAAGCAAGTTGTAGCTC (SEQ ID NO: 24) |
| IFNα1 | Human | GCCTCGCCCTTTGCTTTACT (SEQ ID NO: 25) | CTGTGGGTCTCAGGGAGATCA (SEQ ID NO: 26) |
| IFNα7 | Human | AGGGCCTTGATACTCCTGG (SEQ ID NO: 27) | TCCTCCTCCGGGAATCTGAAT (SEQ ID NO: 28) |
| IFNλ1 | Human | TCGGTAACTGACTTGAATGTCCA (SEQ ID NO: 29) | TCGCTIVCCTGTITTAGCTGC (SEQ ID NO: 30) |
| OAS1 | Human | TGTCCAAGGIGGTAAAGGGTG (SEQ ID NO: 31) | CCGGCGATTTAACTGATCCTG (SEQ ID NO: 32) |
| MX1 | Human | GTTTCCGAAGTGGACATCGCA (SEQ ID NO: 33) | CTGCACAGGTTGTTCTCAGC (SEQ ID NO: 34) |
| IP10 | Human | GTGGCATTCAAGGAGTACCTC (SEQ ID NO: 35) | TGATGGCCTTCGATTCTGGATT (SEQ ID NO: 36) |
| HA | H1N1 influenza | GGCCCAACCACAACACAAAC (SEQ ID NO: 37) | AGCCCTCCTTCTCCGTCAGC (SEQ ID NO: 38) |
| NP | H1N1 influenza | TGTGTATGGACCTGCCGTAGC (SEQ ID NO: 39) | CCATCCACACCAGTTGACTCTTG (SEQ ID NO: 40) |
| MP | H1N1 influenza | CTTCTAACCGAGGTCGAAACGTA (SEQ ID NO: 41) | GGTGACAGGATTGGTCTTGTCTTTA (SEQ ID NO: 42) |

Western Blot:

The cells and homogenized lung tissue were lyzed in M-PER Mammalian Protein Extraction Reagent containing 1% Halt Protease and Phosphatase Inhibitor Cocktail (Pierce, Rockford, Ill.) by Dounce homogenization followed by sonication and freeze/thaw cycles. The proteins were separated by 10% SDS-PAGE and transferred to nitrocellulose membranes. The blots were blocked for 1 hour at room temperature with 5% dried milk in Tris-buffered saline (10 mM Tris/HCl, 100 mM NaCl and 0.05% TWEEN®; pH 7.5) (TBS-T) and incubated overnight at 4° C. with anti-Axin1 (1:1000, Cell Signaling Technology, Danvers, Mass.), anti-Axin2 (1:1000, Cell Signaling Technology, Danvers, Mass.), anti-p-JNK1 (1:1000, Cell Signaling Technology, Danvers, Mass.), anti-JNK1 (1:1000, Cell Signaling Technology, Danvers, Mass.), anti-p-STAT1 (Tyr 701) (1:1000, Cell Signaling Technology, Danvers, Mass.), anti-STAT1 (1:1000, Cell Signaling Technology, Danvers, Mass.), anti-p-GSK-3β (S9) (1:1000, Cell Signaling Technology, Danvers, Mass.), anti-GSK-3β (1:2000, BD Transduction Laboratories, San Jose, Calif.), anti-p-c-Jun (1:1000, Cell Signaling Technology, Danvers, Mass.), anti-c-Jun (1:1000, Cell Signaling Technology, Danvers, Mass.), anti-p-ATF2 (1:1000, Cell Signaling Technology, Danvers, Mass.), anti-ATF2 (1:1000, Cell Signaling Technology, Danvers, Mass.), anti-nonO/p54(nrb) (1:1000, SIGMA, St. Louis, Mo.), anti-SFPQ (1:200, Santa Cruz Biotechnology, Santa Cruz, Calif.), anti-hnRNP M (1:200, Santa Cruz Biotechnology, Santa Cruz, Calif.), anti-c-myc (1:2000, DHSB, Iowa City, IA.), and anti-β-actin (1:2000, SIGMA, St. Louis, Mo.) antibodies. The blots were then rinsed in TBS-T, and incubated for 1 hour at room temperature with goat anti-rabbit, or goat anti-mouse secondary antibodies, coupled to horseradish peroxidase (1:2000, Jackson Immunoresearch, West Grove, Pa.). After being washed, the blots were developed by SuperSignal West Pico Chemiluminescent Substrate (Pierce, Rockford, Ill.). The densities of bands on the scanned film were quantified by ImageJ software (National Institutes of Health, Bethesda, Md. (see the website located at rsb.info.nih.gov/ij).

TCID50 Assay:

MDCK cells in 96-well plates were infected with serial dilutions ($10^{-1}$ to $10^{-7}$) of virus samples in serum-free complete EMEM containing 1 µg/ml TPCK-treated trypsin for 1 hour. The cells were re-fed with the same medium for 4 days. $TCID_{50}$ values (median tissue culture infective dose) were calculated by the method of Reed and Muench.

Immunofluorescence:

A549 cells were cultured on 24-well tissue culture plates. At the end of the experiment, the cells were briefly washed with ice-cold phosphate buffered saline (PBS) and fixed with 4% paraformaldehyde for 15 min in room temperature. After being washed with PBS again, the cells were permeabilized with 0.3% Triton X-100 for 10 min and blocked with 10% FBS for 1 hour at room temperature. After being rinsed, the cells were incubated overnight with primary antibodies against Axin1 (1:200), nonO/p54(nrb) (1:200), SFPQ (1:50), and hnRNP M (1:50). Subsequently, cells were washed with PBS and incubated with Alexa 568-conjugated goat anti-mouse and Alexa 488-conjugated goat anti-rabbit IgG (Invitrogen, Carlsbad, Calif.) for 1 hour. The nuclei were counterstained with 4',6-diamidino-2-phenylindole (DAPI, 1:1000, Invitrogen, Carlsbad, Calif.) for 2 min. Images were acquired using a Nikon Eclipse TE-2000 inverted fluorescence microscope.

Immunoprecipitation:

Cells were lysed in the M-PER mammalian protein extraction reagent (supplemented with 1% Halt phosphatase and proteases inhibitor mixtures). The cell lysate (400 µg of protein) was incubated with anti-Axin1 antibody (2 µg) or control rabbit IgG (2 µg, Cell Signaling Technology, Danvers, Mass.) at 4° C. for 1 h. Then 5 µl of protein A and 10 µl of protein G-agarose beads were added to the mixtures and incubated overnight at 4° C. by gentle end-to-end mixing. The agarose beads were washed three times with ice-cold PBS. The proteins were eluted by boiling in 1×SDS sample buffer for western blot analysis.

Statistics Analysis:

The results were analyzed by one-way ANOVA followed with posthoc Tukey's test for multiple comparisons of control and treatment groups, or Student's t-test using GraphPad Prism (version 6). Survival rates between groups were analyzed by Mantel-Cox $\chi2$ test on Kaplan-Meier probability estimates using GraphPad Prism. All results were reported as mean±s.e.m. (n=3-8 for each condition).

Results: Axin1 is Degraded During Influenza Viral Pneumonia:

A mouse model of viral pneumonia caused by a sub-lethal dose of H1N1 influenza virus infection was used. Weight loss was noticed on day 1 and markedly increased after day 5 (FIG. 1A). The same trend was observed in protein concentration (FIG. 1B) and LDH activity (FIG. 1C) of BAL, indicating vascular leakage and loss of epithelial-endothelial barrier. This observation was also confirmed in histological section (FIG. 1D), in which massive immune cells infiltration can be identified. The number of neutrophils in BAL significantly increased at Day 3 and persisted until day 7 (FIG. 1E). This could inevitably cause alveolar-capillary damage as observed. While macrophage numbers were increased from day 5, infiltration of lymphocyte started from day 6 and this represented the transition from innate immunity to adaptive immunity. To assess the viral replication, viral gene expression including hemagglutinin (HA) was further measured, nucleoprotein (NP) and matrix protein (MP). The expression of all three viral genes reached a plateau at day 3 (FIG. 2A), suggesting that the viral load reached maximum at day 3. IFN response was initiated from day 1 as indicated by increase in mRNA expression (FIG. 2B). As a potential antiviral host factor, Axin1 protein, but not mRNA, expression in the whole lung tissue was significantly reduced at day 1 (FIG. 3), suggesting that Axin1 is degraded in the lung at an early stage of influenza viral pneumonia.

Figure 4:
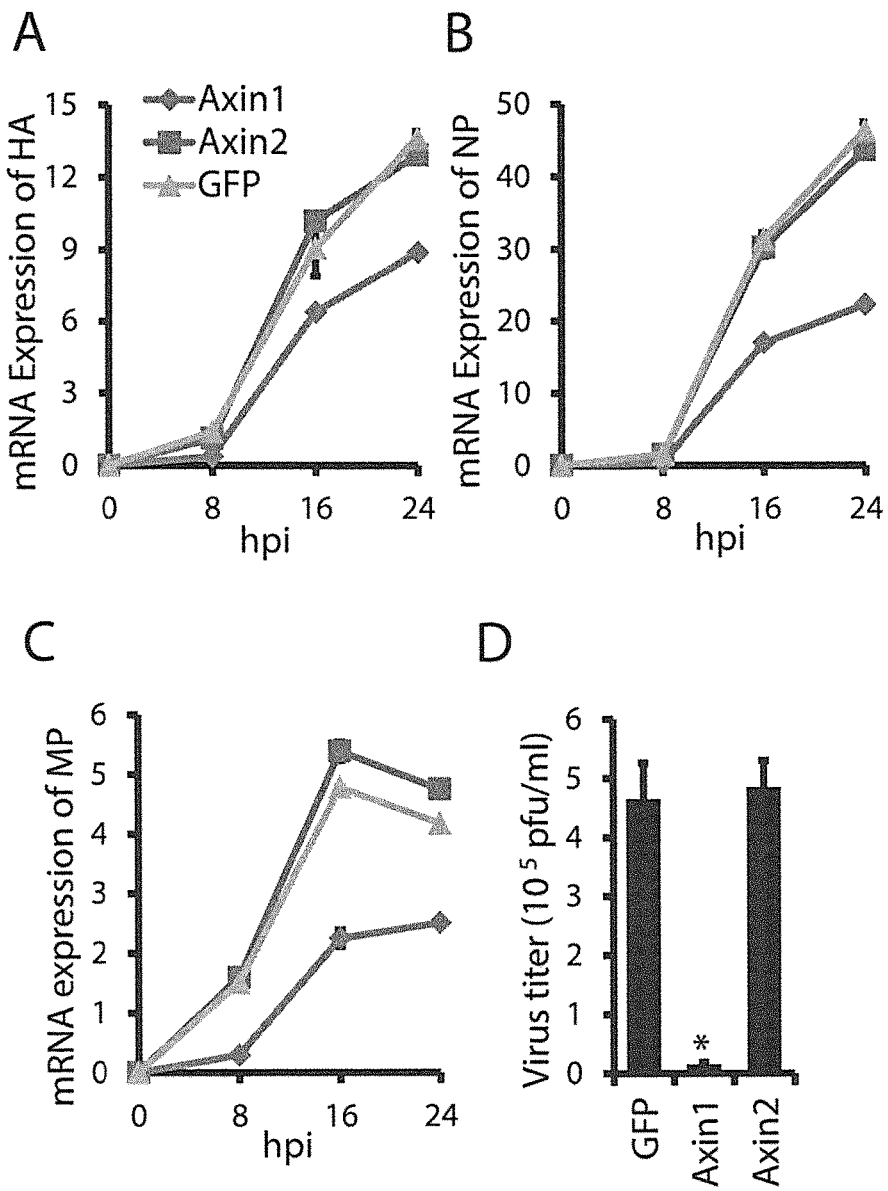
FIG. 4A-D. Axin1 inhibits influenza virus replication. HEK293 cells were transfected with OE-GFP, OE-Axin1, or OE-Axin2 plasmids for 24 hours and then infected with H1N1 influenza A/PR/8/34 virus (MOI=2). The cells were collected at 8 to 24 hours post infection (hpi). (A-C) mRNA expression of viral genes (HA, NP, and MP) were analyzed by Real-time PCR and normalized to β-actin. (D) Virus titer in the supernatants (24 hpi) was measured by TCID50 assay in MDCK cells. Values represent means±s.e.m. of three independent experiments and statistical significance determined by one-way ANOVA analysis with posthoc Tukey's test. *$P<0.001$ vs. OE-GFP.
Figure 5:
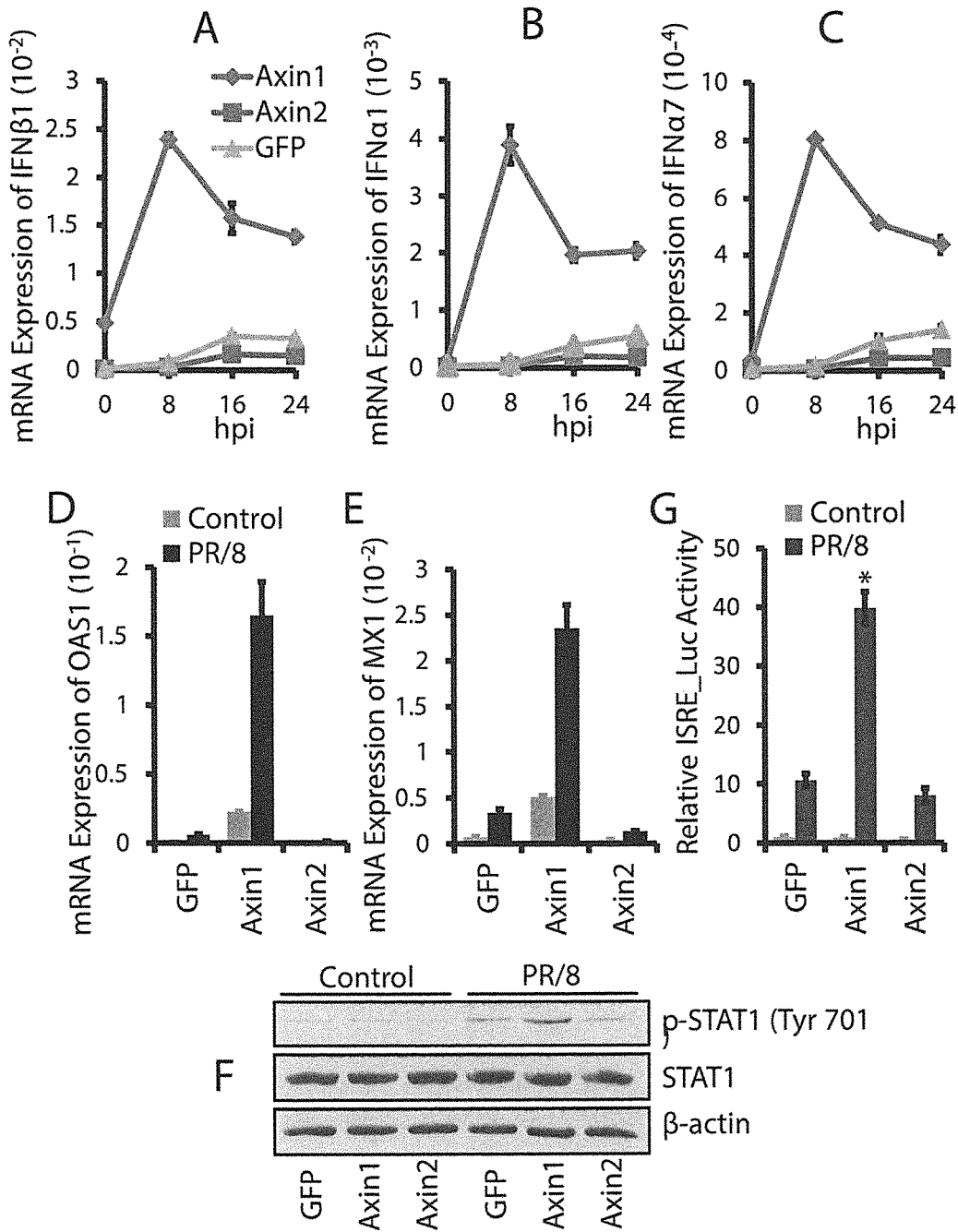
FIG. 5A-G. Axin1 stimulates type I IFN response during influenza virus infection. HEK293 cells were transfected with OE-GFP, OE-Axin1, or OE-Axin2 plasmids for 24 hours and then infected with H1N1 influenza A/PR/8/34 virus (MOI=2) for indicated time. mRNA expressions of (A-C) type I IFN (IFNβ1, IFNα1, and IFNα7) and (D-E) type I IFN-stimulated genes (OAS1 and MX1) (8 hpi) were measured by Real-time PCR and normalized to β-actin. (F) Western blot was carried out to determine the protein expression of p-STAT1 (Tyr 701) and total STAT1 with and without virus infection (2 hpi). The expression of β-actin was used as an internal control. ISRE_Luc and pRL-TK plasmids were transfected into HEK293 cells together with OE-GFP, OE-Axin1, or OE-Axin2 plasmids for 24 hours. Cells were then infected with H1N1 influenza A/PR/8/34 virus (MOI=2) for 8 hours. (G) Dual-luciferase assay was performed and the results were expressed as the ratio of ISRE_Luc Firefly luciferase activity to pRL-TK Renilla luciferase activity. Data shown are means±s.e.m. of three independent experiments and tested for statistical significance by ANOVA analysis with posthoc Tukey's test. *$P<0.01$ v.s. OE-GFP.
Figure 12:
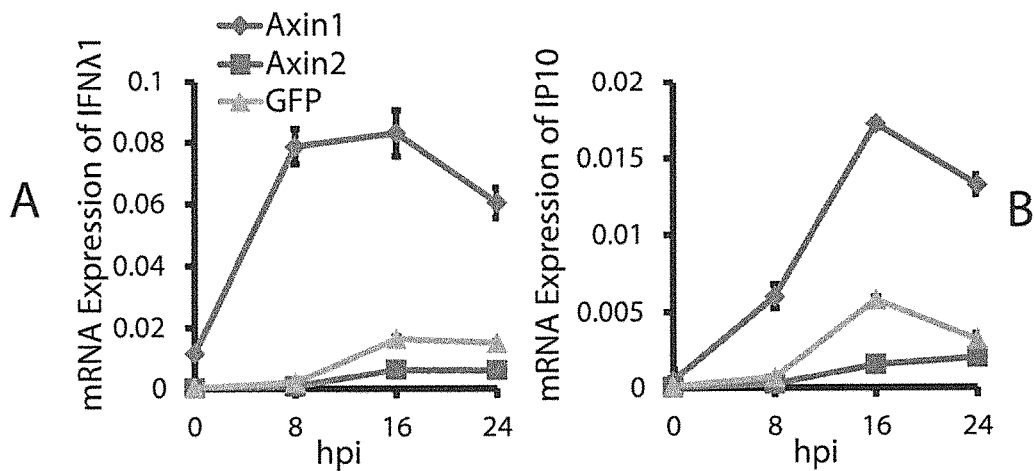
FIGS. 12A and B. Axin1 elevates type III IFN response during influenza virus infection. OE-GFP, OE-Axin1, or OE-Axin2 plasmids were transfected into HEK293 cells. One day after transfection, cells were infected with H1N1 influenza A/PR/8/34 virus (MOI=2) for indicated time. mRNA expression of (A) type III IFN (IFNλ1) and (B) type III IFN-induced gene (IP10) as measured by Real-time PCR and normalized to β-actin. Values represent as means±s.e.ms of three independent experiments.

Axin1 Inhibits Influenza Virus Replication Through Boosting IFN Response:

To evaluate the potential role of Axin1 in regulating influenza virus replication, Axin1 or Axin2 in HEK293 were overexpressed cells prior to virus infection. Axin1 but not Axin2 inhibited viral gene amplification (FIGS. 4A, B and C) and virus replication (FIG. 4D). Axin1 successfully boosted type I IFN mRNA expression including IFNβ1 (FIG. 5A), IFNα1 (FIG. 5B), and IFNα7 (FIG. 5C). Accordingly, Axin1 also significantly augmented the expression of type I IFN-targeted anti-viral genes, including OAS1 (FIG. 5D) and MX1 (FIG. 5E). Axin1 also elevated type III IFN (IFNλ1) synthesis and response (FIG. 12). STAT1, the transcription factor essential for turning on ISGs expression, was activated by Axin1 (FIG. 5F). The activity of interferon-sensitive responsive element (ISRE), primarily responsible for the constitutive expression of ISGs, was notably increased as well (FIG. 5G). This result indicated that the cellular anti-viral machinery was turned on by Axin1.

Figure 6:
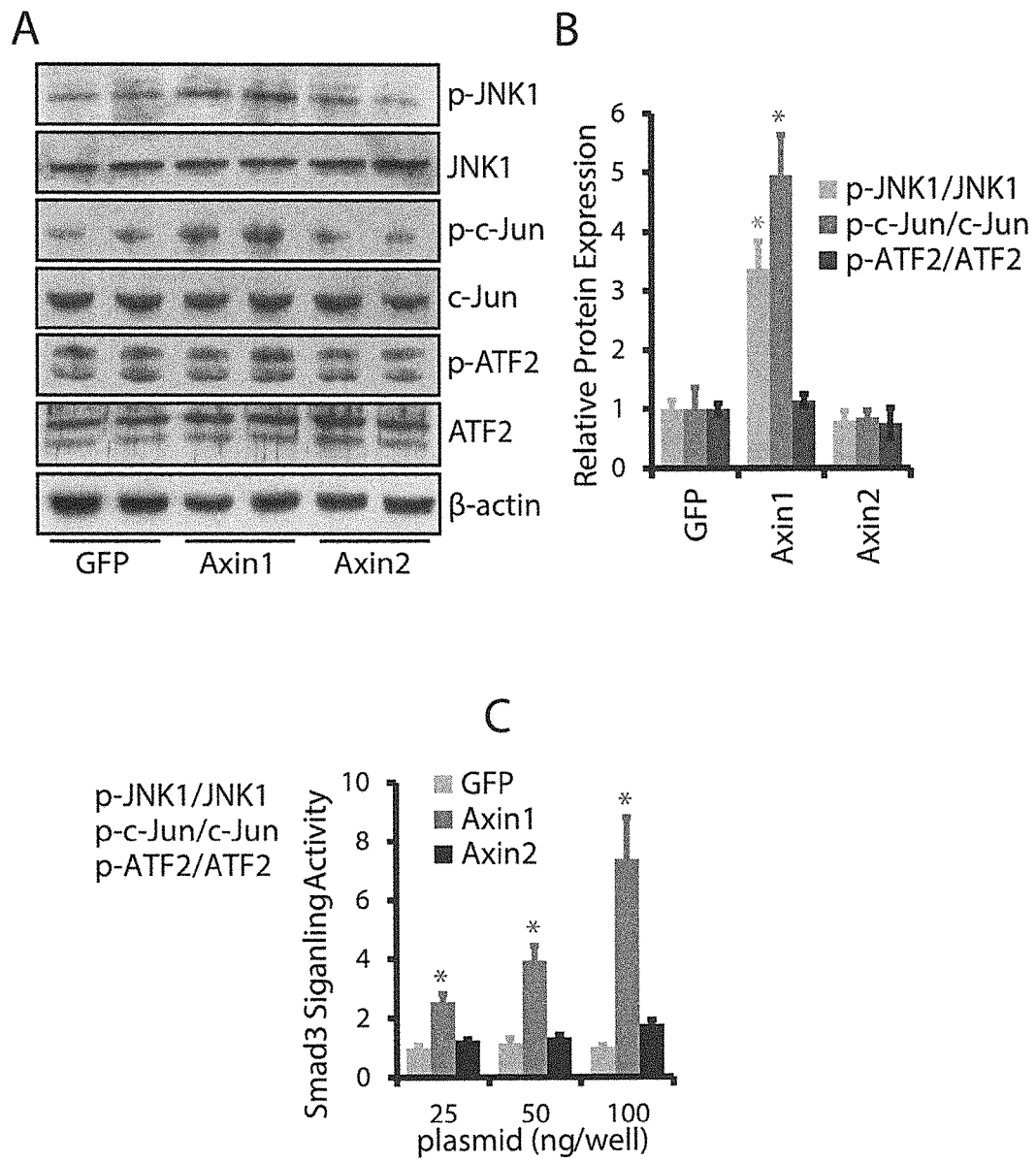
FIG. 6A-C. Axin1 activates JNK/c-Jun pathway and Smad3 signaling. (A) HEK293 cells were transfected with OE-GFP, OE-Axin1, or OE-Axin2 plasmids for 24 hours. The protein levels of phosphorylated JNK1 (p-JNK), total JNK (JNK), phosphorylated c-Jun (p-c-Jun), total c-Jun (Jun), phosphorylated ATF2 (p-ATF2), and total ATF2 (ATF2), were determined by Western blot. (B) Relative band intensities of phosphorylated proteins were quantified and normalized to respective total proteins. (C) Smad3 signaling reporter and pRL-TK plasmids were transfected together with different doses of OE-GFP, OE-Axin1, or OE-Axin2 plasmids into HEK293 cells for 24 hours. Dual-luciferase assay was performed. The results were expressed as a ratio of Smad3 signaling reporter Firefly luciferase activity to pRL-TK *Renilla* luciferase activity. Data shown are means±s.e.m. of three independent experiments, and statistical significance determined by one-way ANOVA analysis with posthoc Tukey's test. *$P<0.01$ v.s. OE-GFP.
Figure 7:
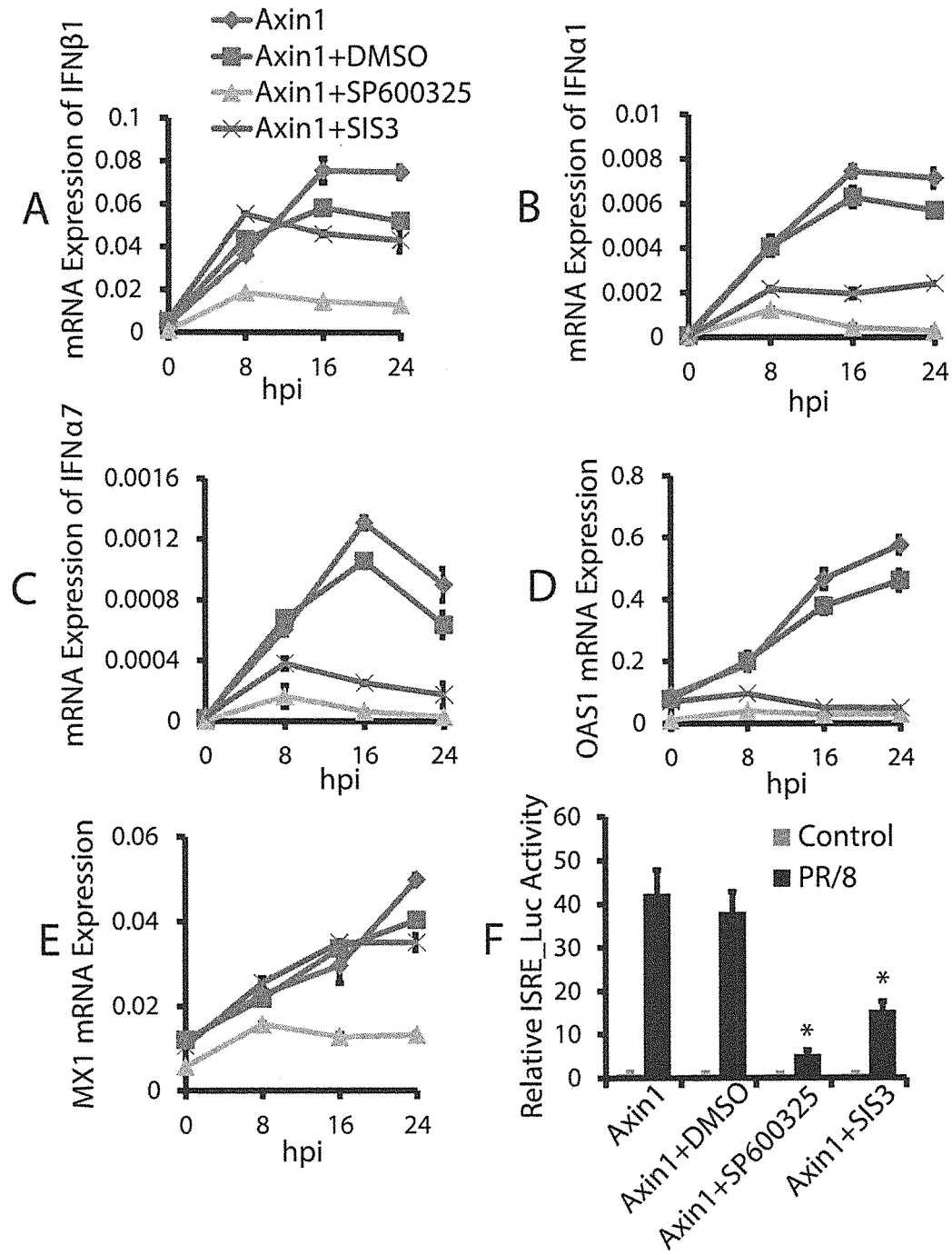
FIG. 7A-F. Inhibition of JNK/c-Jun and Smad3 signaling reduces Axin1-stimulated type I IFN response. HEK293 cells were pretreated with 10 μM SP600125 (JNK inhibitor), 10 μM SIS3 (Smad3 inhibitor), or 0.05% DMSO for 6 hours. The cells were then transfected with OE-Axin1 plasmid for 24 hours and then infected with H1N1 influenza A/PR/8/34 virus (MOI=2) for indicated times. The mRNA expression of (A-C) type I IFN (IFNβ1, IFNα1, and IFNα7) and (D-E) type I IFN-stimulated genes (OAS1 and MX1) was measured by Real-time PCR and normalized to β-actin. (F) HEK293 pretreated with indicated inhibitors cells were transfected with ISRE_Luc and pRL-TK plasmids together with OE-Axin1 plasmid for 24 hours. Cells were then infected with H1N1 influenza A/PR/8/34 virus (MOI=2) for 8 hours. Dual-luciferase assay was carried out and the ISRE_Luc Firefly luciferase activity was normalized to pRL-TK *Renilla* luciferase activity. Data shown are means±s.e.m. and tested for statistical significance by ANOVA analysis with posthoc Tukey's test. *$P<0.05$ vs. OE-Axin1+DMSO.
Figure 13:
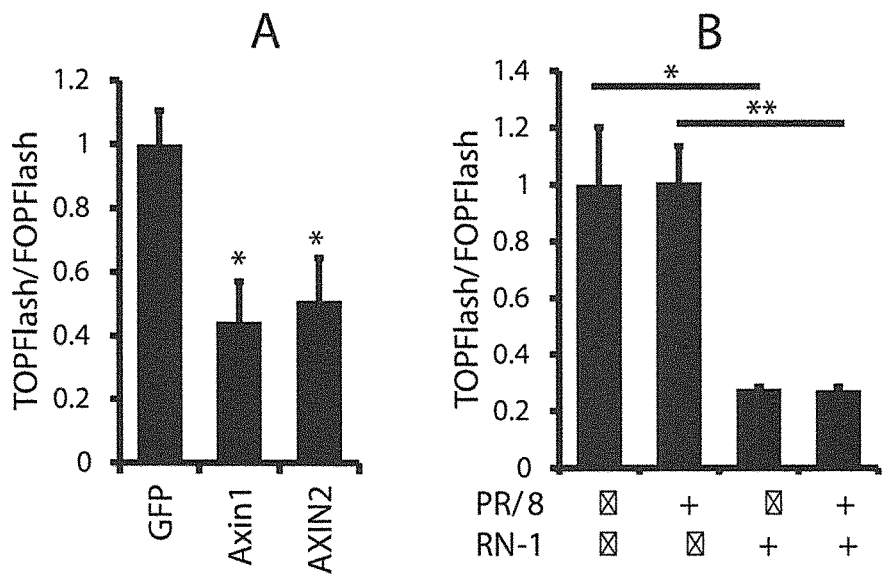
FIGS. 13A and B. Axin and its stabilizer RN-1 inhibit Wnt/β-catenin signaling. (A) TOPFlash\FOPFlash and pRL-TK plasmids were transfected together with OE-GFP, OE-Axin1, or OE-Axin2 plasmids into HEK293 cells for 24 hours. (B) A549 cells were transfected with TOPFlash\FOPFlash and pRL-TK plasmids for 12 hours and then treated with RN-1 for 24 hours. After that, cells were infected with H1N1 influenza A/PR/8/34 virus (MOI=2) for 12 hours. Dual-luciferase assay was performed. TOPFlash or FOPlash Firefly luciferase activity was normalized to pRL-TK *Renilla* luciferase activity. The results were expressed as the ratio of normalized TOPFlash to FOPlash activity. Data shown are means±s.e.m. of three independent experiments and tested for statistical significance by one-way ANOVA analysis with posthoc Tukey's test. *$P<0.05$ v.s. OE-GFP.
Figure 14:
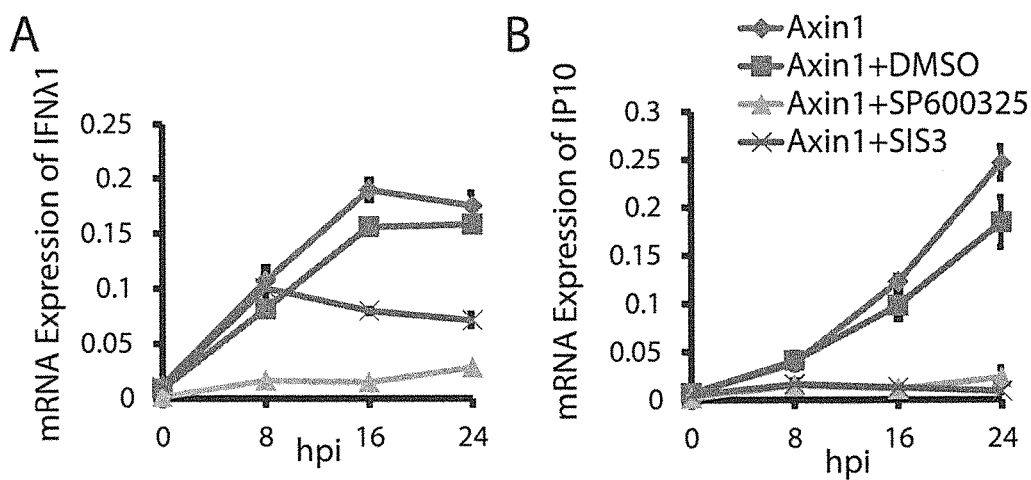
FIGS. 14A and B. Blockage of JNK/c-Jun pathway and Smad3 signaling attenuates Axin1-elevated type III IFN response. HEK293 cells were pretreated with 10 μM SP600125 (JNK inhibitor), 10 μM SIS3 (Smad3 inhibitor), or 0.05% DMSO. 6 hours later, the cells were transfected with OE-Axin1 plasmid for 24 hours and then infected with H1N1 influenza A/PR/8/34 virus (MOI=2) for indicated times. mRNA expression of (A) type III IFN (IFNλ1) and (B) type III IFN-induced gene (IP10) as measured by Real-time PCR and normalized to β-actin. Values represent as means±s.e.m of three independent experiments.
Figure 15:
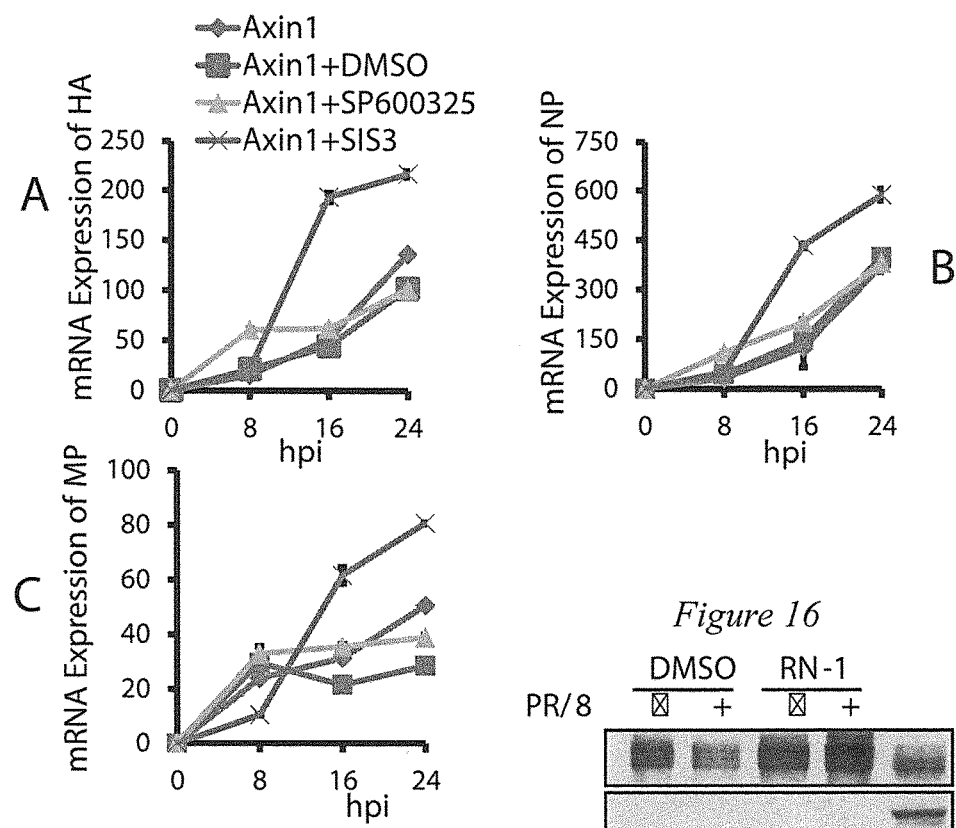
FIG. 15A-C. Inhibition of Smad3 signaling relives Axin1-mediated attenuation of influenza virus replication. HEK293 cells were pretreated with 10 μM SP600125 (JNK inhibitor), 10 μM SIS3 (Smad3 inhibitor), or 0.05% DMSO for 6 hours. The cells were transfected with OE-Axin1 plasmid for 24 hours and then infected with H1N1 influenza A/PR/8/34 virus (MOI=2) for indicated times. mRNA expression of viral genes (A, HA; B, NP; and C, MP) were analyzed by Real-time PCR with β-actin as a reference. Values represent as means±s.e.m of three independent experiments.

JNK/c-Jun and Smad3 Mediate Axin1-Stimulated IFN Response:

To further study the mechanism of Axin1-mediated stimulation of IFN response, cell signaling affected only by Axin1 (including TGF-β/Smad, JNK/c-Jun, and p53 signaling) was investigated. Both Axin1 and Axin2 inhibited canonical Wnt/β-catenin signaling assessed by TOPflash assay (FIG. 13A). This is consistent with their accordant function in the β-catenin degradation complex. However, Axin1 specifically activated JNK/c-Jun pathway by increasing the phosphorylation of both JNK1 and c-Jun without changing ATF2 (FIGS. 6A and B). Axin1, but not Axin2, also triggered the activation of Smad3 signaling (FIG. 6C). SP600125, a specific JNK inhibitor, successfully blocked Axin1-stimulated IFN mRNA expression (FIGS. 7A-C and 14A), ISGs expression (FIGS. 7D, E, and 14B) and ISRE activity (FIG. 7F). SIS3, a specific Smad3 inhibitor, exhibits the same inhibitory effect on Axin1-elevated anti-viral machinery except IFNβ1 synthesis (FIG. 7A) and MX1 expression (FIG. 7E). However, only SIS3 not SP600125 relived Axin1-mediated attenuation of influenza virus replication (FIG. 15). This result showed that both the JNK/c-Jun pathway and Smad3 signaling participated in Axin1-stimulated IFN response, albeit through different mechanisms.

Figure 16:
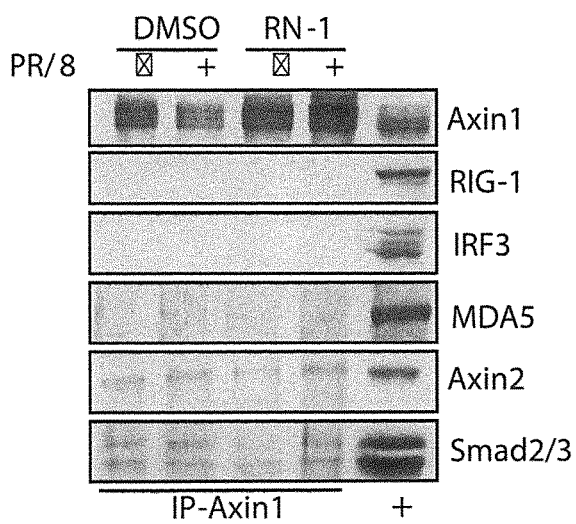
FIG. 16. Axin1 interaction partners in the RIG-1 pathway. A549 cells were pretreated with 20 μM RN-1 or 0.05% DMSO for 24 hours. Cells were then infected with H1N1 influenza A/PR/8/34 virus (MOI=2) for 24 hours. Axin1 was pulled down from lysed cells by immunoprecipitation and probed with indicated antibodies by Western blot using Axin2 and Smad2/3 as positive control.

Axin1 Interacts with Novel Viral RNA Sensor:

To further explore the details of Axin1-mediated activation of the IFN response, potential physical interactions between Axin1 and classic viral RNA sensors that function in the RIG-1-like pathway were analyzed. Axin1 did not interact with RIG-1 and MDA5 (FIG. 16). However, using mass spectrometry, Axin1 was surprisingly identified as interacting with IFIT1/2/3, a novel IFN-induced viral RNA sensor complex, during influenza virus infection (Table 2). These results brought Axin1 into the antiviral network of interferon as a scaffold protein.

Figure 8:
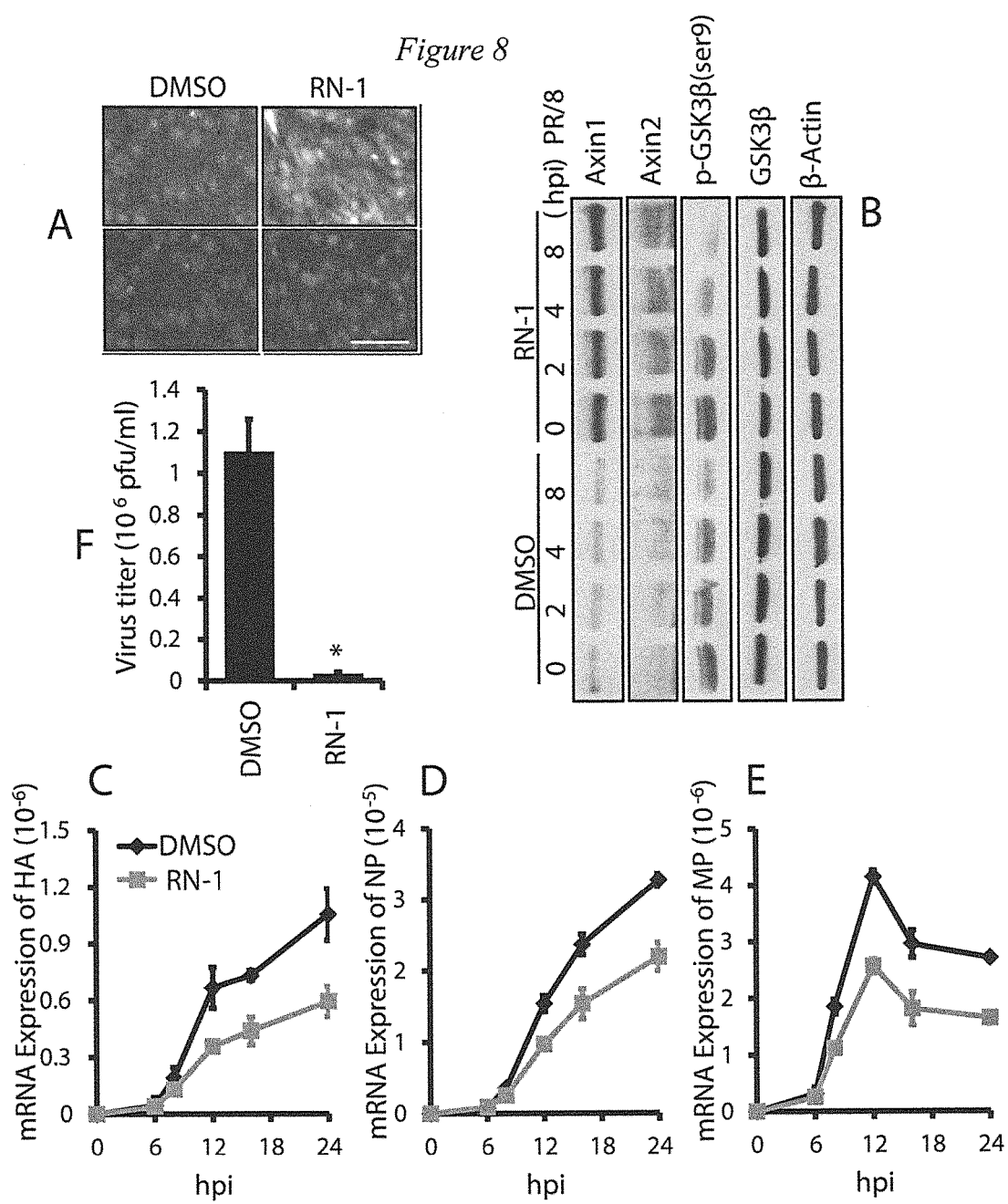
FIG. 8A-F. RN-1 stabilizes Axin1 and inhibits influenza virus replication in A549 cells. A549 cells were pretreated with 20 μM RN-1 or 0.05% DMSO for 24 hours. Cells were then infected with H1N1 influenza A/PR/8/34 virus (MOI=2) for indicated times. (A) Immunostaining of Axin1 (top row) with DAPI nuclear staining (bottom row) after RN-1 treatment, (Scale bar=50 μm). (B) Western blot analysis of the indicated protein expression. (C-E) mRNA expression of viral genes (HA, NP, and MP) as analyzed by Real-time PCR and normalized to 18S rRNA. (F) Virus titer in the supernatants (24 hpi) was measured by standard TCID50 assay in MDCK cells. Values represent means±s.e.m. of three independent experiments and statistical significance determined by Student's t-test. *$P<0.001$ v.s. DMSO.
Figure 9:
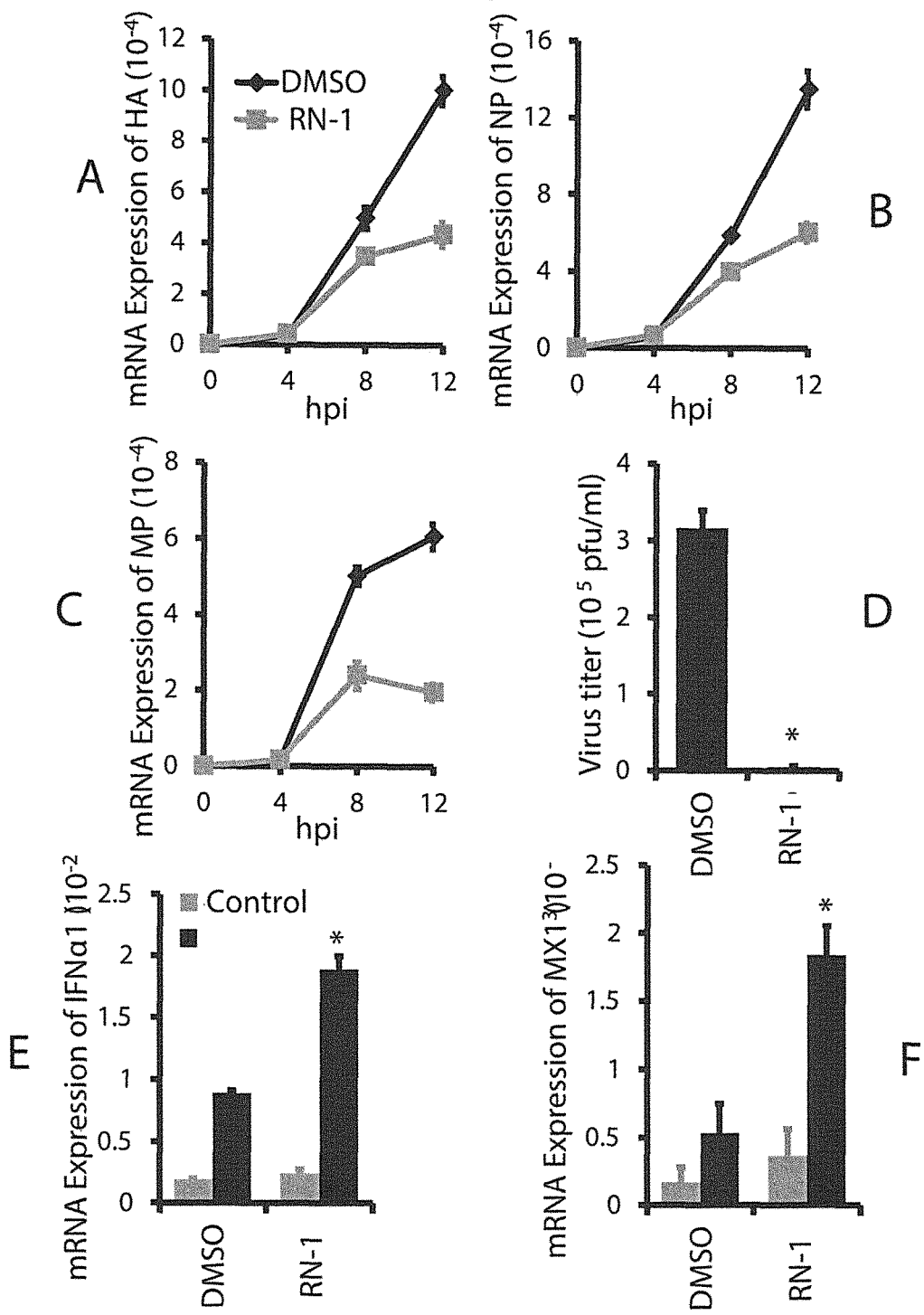
FIG. 9A-F. RN-1 reduces influenza virus replication and augments type I IFN response in primary mouse alveolar epithelial cells. Primary mouse alveolar epithelial cells were pretreated with 20 μM RN-1 or 0.05% DMSO for 24 hours. Cells were then infected with H1N1 influenza A/PR/8/34 virus PR/8 (MOI=2) for indicated times. (A-C) mRNA expression of viral genes (HA, NP, and MP) were analyzed by Real-time PCR and normalized to 18S rRNA. (D) Virus titer in the supernatants (24 hpi) was measured by TCID50 assay in MDCK cells. mRNA expression of IFNα1 (E) and MX1 (F) (12 hpi) were measured by Real-time PCR and normalized to β-actin. Data shown are means±s.e.m. of three independent experiments and tested for statistical significance by one-way ANOVA analysis with posthoc Tukey's test or Student's t-test. *$P<0.05$ v.s. DMSO.

RN-1 Stabilizes Axin1 and Attenuates Influenza Virus Replication In Vitro:

To further validate the role of Axin1 against virus replication, RN-1, a tankyrase inhibitor, was utilized to stabilize Axin1 in A549 cells (FIGS. 8A and B). Axin1 was not degraded during influenza virus infection in A549 cells when RN-1 was present (FIG. 8B). In addition, RN-1 significantly attenuated influenza viral gene expression (FIG. 8C-E) and virus replication (FIG. 8F) in A549 cells. RN-1 also notably inhibited influenza viral gene expression (FIG. 9A-C) and virus replication (FIG. 9D) in primary mouse alveolar epithelial cells. Accordingly, RN-1 increased IFNα1 (FIG. 9E) and MX1 (FIG. 9F) expression during virus infection in primary mouse alveolar epithelial cells.

Figure 10:
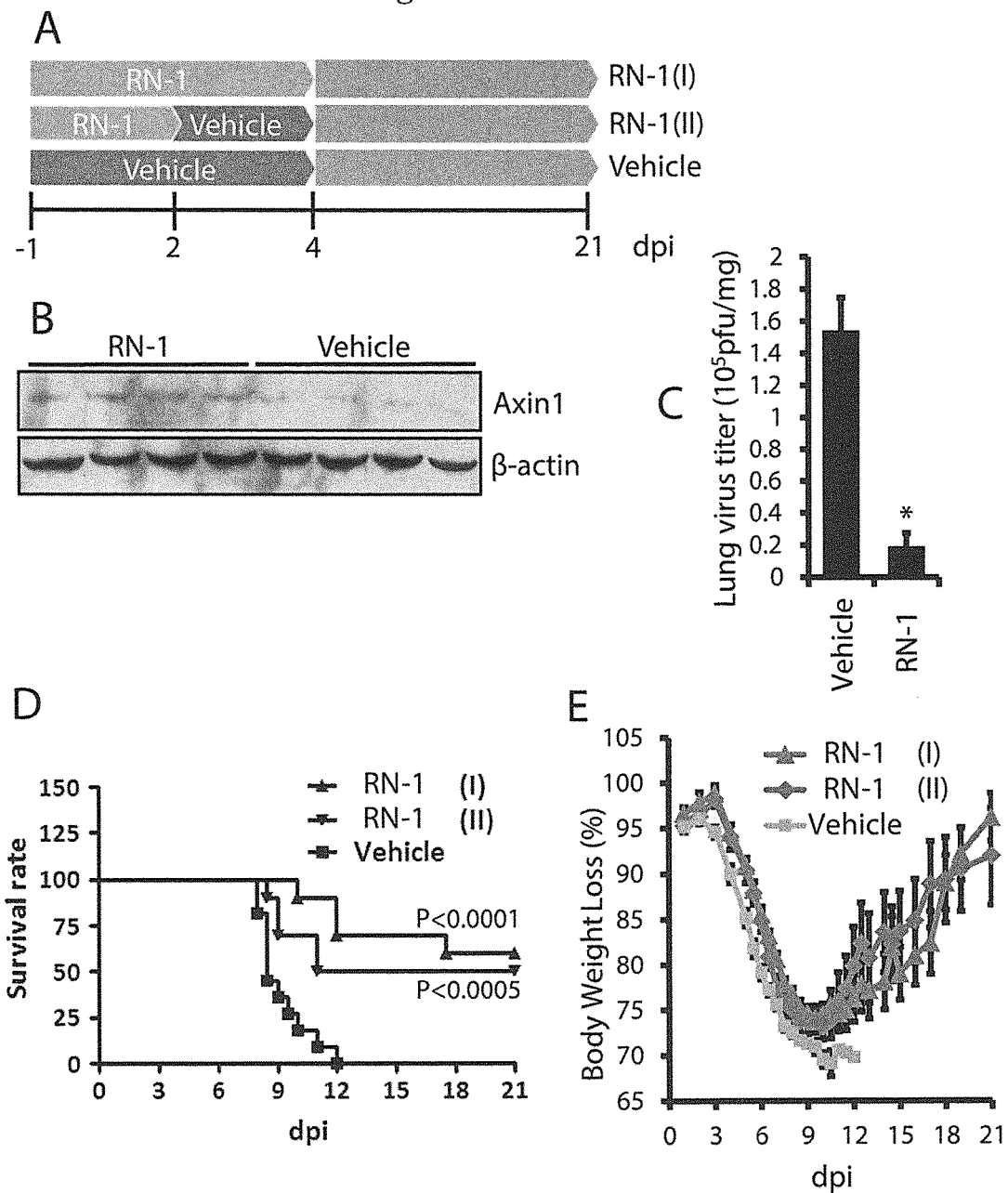
FIG. 10A-E. RN-1 stabilizes Axin1 and protects mice from lethal virus challenge. Mice were challenged intranasally with a lethal dose (1,000 pfu) of H1N1 influenza A/PR/8/34 virus. RN-1 treatment was given orally and daily, beginning with one day before infection (−1 dpi) and continued until 2 (RN-1 (I)) or 4 (RN-1 (II)) days post infection. Control animals received vehicle alone. (A) The illumination of experiment design. (B) Axin1 protein expression in the lungs after 24 hours oral treatment of RN-1. (C) Virus titer in the homogenized infected lungs at 2 dpi was measured by TCID50 assay in MDCK cells and normalized to total protein amount. (n=5). Data shown are means±s.e.m. and tested for statistical significance by Student's t-test. (D) Survival rate. (E) Body Weight. Mantel-Cox $\chi2$ test on Kaplan-Meier survival data was used to compare the survival rate between groups.

RN-1 Protects Mice from Lethal Virus Challenge:

To evaluate the therapeutic application of Axin1 as a novel target to limit virus infection, RN-1 was further tested as a potential antiviral agent in vivo (FIG. 10A). Oral administration of RN-1 for 24 hours successfully stabilized Axin1 in the mouse lung as previously reported (FIG. 10B). RN-1 also significantly attenuated influenza virus replication in vivo (FIG. 10C) and dramatically improved the survival rate of animals challenged with a lethal dose of the virus at 1,000 pfu/mice with two different strategies of RN-1 administration (−1 to 2 and 4 dpi) (FIG. 10D).

Axin1 interacts with host factors involved in antiviral response.

As a scaffold protein, Axin1 could potentially interact with other host factors and be incorporated into other cellular antiviral machinery against influenza virus replication. Besides regulating IFN responses, Axin1 was also found to be colocalized with and to interact with three other host factors (nonO/p54(nrb), SFPQ, and hnRNP M) that are involved in antiviral responses (FIG. 17). RN-1 stimulated the degradation of all three proteins (FIG. 18A). Then, more detailed experiments found that Axin1 and Axin2 both facilitated the degradation of nonO/p54(nrb) and SFPQ during influenza virus infection (FIG. 18B). However, Axin1 specifically promoted the degradation of hnRNP during viral infection (FIG. 18B). These results suggest that hnRNP M could be essential for influenza virus replication.

Discussion

Figure 11:
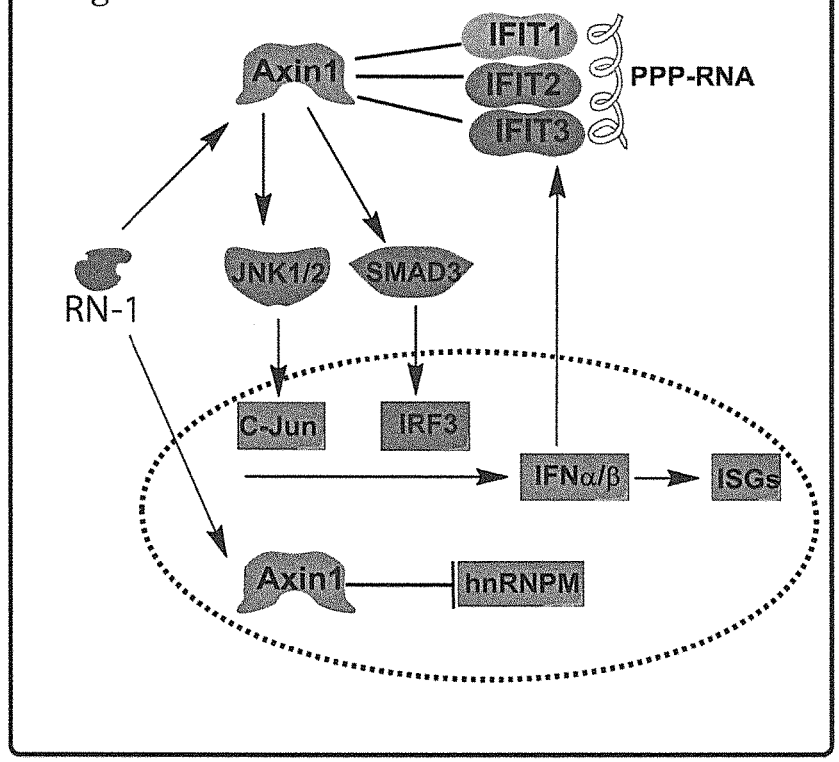
FIG. 11. Axin1 joins the antiviral network of interferon. Axin1 interacts with viral RNA sensor IFIT1/2/3 to initialize the type I IFN response against influenza virus replication through JNK/c-Jun and Smad3/IRF3 signaling. Axin1 also specifically promotes the sequential degradation of hnRNP M, an essential host factor supporting influenza virus replication. As such, RN-1, Axin stabilizer, could be used as a potential broad-spectrum inhibitor against virus infection.

The mortality rate of pneumonia and influenza virus infection continually declined through the 20th century because of the improvement of anteceded medical strategies for prevention of lung infections. However, acute pulmonary infection remains a substantial concern as acute lower respiratory infections still cause the most deaths and are the largest economic burden among all infectious diseases worldwide. Influenza virus has the ability to span on patients of all ages even adults. In the course of this work, protective effect of Axin1 and its stabilizer RN-1 on influenza virus infection was determined. By interacting with IFIT1/2/3, a novel RNA virus sensor complex, Axin1 boosts antiviral type I IFN response through augmenting JNK/c-Jun and Smad3 signaling. Axin1 also interacts and promotes the degradation of hnRNP M, an essential host factor for influenza virus replication, sequentially (FIG. 11). Targeting Axin1 to regulate IFN response represents potential broad-spectrum antivirals.

A unique feature in signaling transduction is that several different pathways depend on a group of crucial regulators referred to as scaffolds, which bind simultaneously several components in the same or different signaling routes and augment specificity and efficacy during signal transduction. By serving as a multidomain scaffold, Axin1 coordinates several different protein complexes involved in regulating TGF-β/Smad, JNK/c-Jun, and p53 signaling. In the course of this work it was determined that both transcription factors, c-Jun and Smad3, were activated by Axin1 to facilitate IFN response against virus replication. Instead of classic viral RNA sensors, RIG-1 and MAD5, Axin1 was detected through a newly identified viral 5' triphosphate double stranded RNA (5'ppp-dsRNA) sensor complex IFIT1/2/3, which initializes IFN-mediated antiviral response. This positive-regulated signaling cycle mediated by Axin1 and IFIT1/2/3 (ISGs) remains to be determined.

Both IRF3 and IRF7 are well known to be essential for the cytosolic pathway-mediated type I IFN induction. Because Smad3 can only interact and cooperate with IRF7, there is an opportunity to explore the relative contribution of IRF3 and IRF7 to the activation of type I IFN synthesis and ISGs expression. In the recently established "two-step" model, IRF3 is primarily responsible for the initiation of IFNβ1 expression. IRF7 is then induced by IFNβ1 and comes into play in the later phase for IFNαs induction. Our results support this hypothesis because SIS3 (Smad3 inhibitor) only inhibited Axin1-induced expression of IFNα but not IFNβ1. In the same experiment setting, a clear difference between IRF3 and IRF7 in regulating OAS1 and MX1 expression (FIG. 7D, E) was discovered. As expected by the instant inventors, SIS3 successfully relived Axin1-mediated attenuation of virus replication. This result also partially confirmed that the effect of Axin1 on virus replication is through regulating type I IFN response.

In the promoter region of type I IFN genes, the assembly of ATF2 and c-Jun (AP1) is required for their substantial expression. It was discovered that Axin1 only activated JNK/c-Jun pathway without affecting p38/ATF2 activity.

Unlike SIS3, SP600125 (JNK/c-Jun pathway inhibitor) failed to reverse Axin1-inhibited virus propagation even though it inhibited the Axin1-agumented type I IFN responses. This mismatch is probably because JNK/c-Jun pathway inhibitor itself can suppress influenza viral RNA and protein synthesis, and override the effect of attenuated type I IFN responses on virus replication.

Type I and Type III IFN activate the same STAT heterodimer (STAT1/2) to induce ISGs from IFN-stimulated response elements (ISREs). Axin1 significantly stimulated STAT1 and subsequent ISREs activity. Our results reveal the same mechanism of Axin1 on regulating both Type I and Type III IFN synthesis because SIS3 and SP600125 exhibits the same inhibitory effect in both scenarios.

Figure 18:
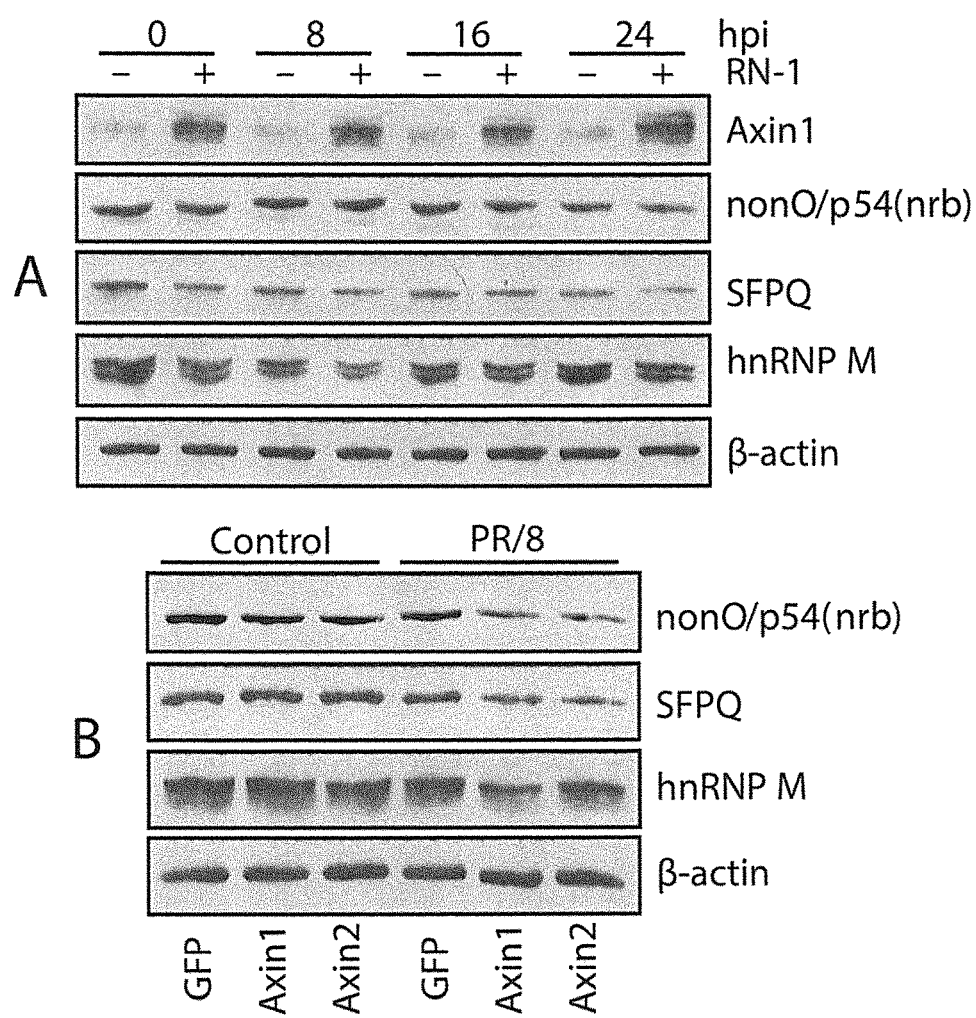
FIGS. 18:A and B. Axin1 specifically facilitates degradation of hnRNP M during influenza virus replication. (A) A549 cells were pretreated with 20 μM RN-1 or 0.05% DMSO for 24 hours. Cells were then infected with H1N1 influenza A/PR/8/34 virus (MOI=2) for indicated time. (B) HEK293 cells were transfected with OE-GFP, OE-Axin1, or OE-Axin2 plasmids for 24 hours and then infected with H1N1 influenza A/PR/8/34 virus (MOI=2) for 2 hours. Western blot was carried out to check the indicated protein expression using β-actin as internal control.
Figure 19:
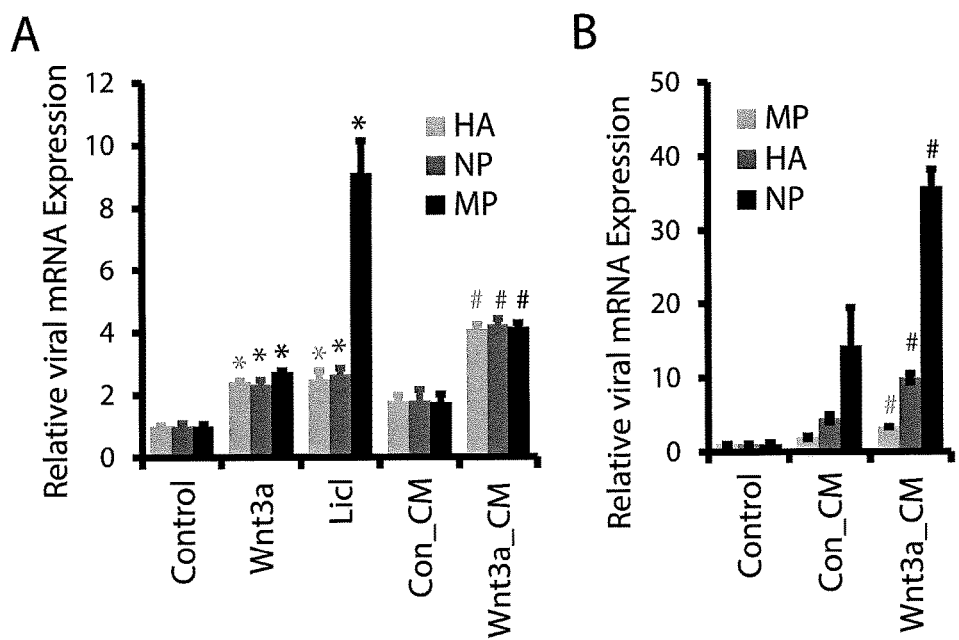
FIGS. 19A and B. Activation of Wnt/β-catenin signaling amplify influenza virus replication. (A) E10 cells were pretreated with 250 ng/ml rhWnt3a, 25 mM LiCl, 50% Con_CM, or 50% Wnt3a_CM for 24 hours. Cells were then infected with H1N1 influenza A/PR/8/34 virus PR/8 (MOI=2) for 18 hours. (B) Mice were inoculated with influenza virus A/Puerto Rico/8/1934 H1N1 (250 pfu) intranasally. 50 µl 10× Wnt3a_CM or Con_CM was given to the mice 4 hours before infection and 2 days post infection intranasally. Lungs were isolated on day 5 post infections. (n=4/group). mRNA expression of viral genes (HA, NP, and MP) were analyzed by Real-time PCR with 18S rRNA as a reference. The results were normalized to control and represent as means±s.e.m. Statistical significance was tested by one-way ANOVA analysis followed by posthoc Tukey's test. *$P<0.01$ v.s. Control. #$P<0.05$ v.s. Con_CM.
Figure 20:
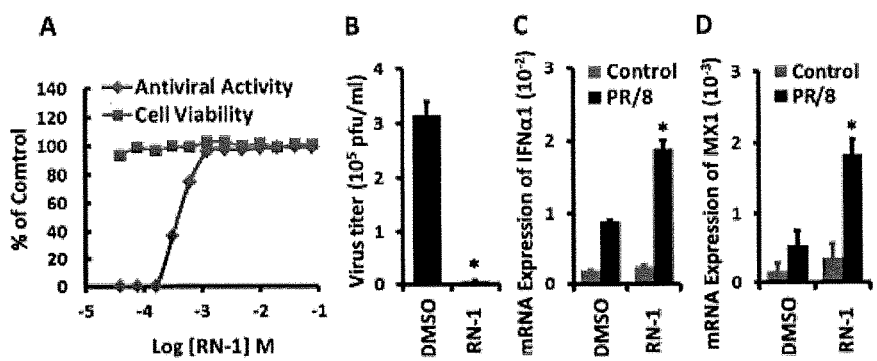
FIG. 20A-D contains Effects of RN-1 on influenza virus infection and IFN response. Virus titers in culture media from vehicle (dimethyl sulfoxide, DMSO) or RN-1-treated A549 cells (30-80,000 nM) (A) and primary mouse alveolar epithelial cells (20 µM) (B) infected with H1N1 influenza A/PR/8/34 virus (PR/8) were determined by $TCID_{50}$ assay. The cell viability (A) was determined by MTT assay. The mRNA expression of IFNα1 (C) and IFN-stimulated gene, MX1 (D) in primary mouse alveolar epithelial cells were measured by Real-time PCR and normalized to β-actin. Data shown are means±SE of three independent experiments. *$P<0.05$ vs. DMSO.

Axin2 did not amplify the type I IFN response and affect virus replication. The similar effect was also observed in bacterial *Salmonella* infection. Considering that both Axin1 and Axin2 inhibited Wnt/catenin signaling (FIG. 13A), the activation of type I IFN synthesis by Axin1 is obviously not through the manipulation of Wnt/catenin signaling. Influenza virus infection also has no effect on Wnt/catenin signaling (FIG. 13B). However, the activation of Wnt/catenin signaling by Wnt3a dramatically promotes virus replication through an unknown mechanism in vitro and in vivo (FIG. 18). Actually, Wnt3a has been reported to amplify IFN response potentially through interaction between β-Catenin and LRRFIP1, another cytosolic viral RNA sensor. However, this cannot explain the remarkable effect of Wnt/catenin signaling on virus amplification. Instead, it implicates the induction of type I IFN synthesis by Axin1 through JNK/c-Jun and Smad3 signaling is intensive enough to override the potential negative effect of suppressed Wnt/catenin signaling on ISREs response. Considering the side effect of type I IFN on sensitizing host to secondary bacterial pneumonia post influenza infection and promoting cell death as Axin1 normally involved, more detailed studies need to be carried out in vivo.

Axin1 has been reported to be the rate limiting factor for the β-catenin destruction complex assembly due to its extremely low basal expression. This unique feature and its antiviral property make it a perfect host factor to be stabilized against virus infection. In this work, RN-1 was utilized to stabilize Axin1 and evaluated its potential antiviral activity against influenza virus in vitro and in vivo. RN-1 has previously been reported to inhibit herpes simplex virus replication. Oral administration of RN-1 successfully stabilizes Axin1 in the lung as previously reported. More importantly, RN-1 successfully reduces influenza virus replication in vitro and in vivo, and protects the mice from lethal influenza virus infection.

IFN exerts significant protection on limiting respiratory virus infection including highly pathogenic H5N1 influenza A virus infection in animals. However, viruses can block nearly all aspects of IFN regulatory pathway through intimate interplay to avoid the compromise of virus replication. It was determined that Axin1, as an antiviral mediator, was degraded in influenza viral pneumonia in vitro but not in vitro. This could be due to complicated systemic response to virus infection, sophisticated paracrine signaling, and an adequate set of protein degradation machinery in vivo. Several other components of ubiquitin-proteasome pathway (USP34 and RNF146) and small ubiquitin-related modifier (SUMO) are also involved in regulating homeostasis of Axin1. Targeting these molecules to stabilize Axin1 could also be potentially utilized against virus replication.

Functional genomics and proteomics have been given a great appreciation to provide broad view of virus-host interactions. Recently, a quantitative proteomics study reveals reduced levels in paraspeckle proteins splicing factor proline-glutamine rich (SFPQ) and Non-POU domain-containing octamer-binding protein (nonO/p54(nrb)) in influenza A virus-infected cells. These proteins are frequently associated with heterogeneous nuclear ribonucleoprotein M (hnRNP M) in defined nuclear structure to influence splicing patterns of specific pre-mRNAs. A recent study further demonstrates that SFPQ, but not nonO/p54(nrb), is a host factor specifically required for influenza virus multiplication by increasing the efficiency of viral mRNA polyadenylation and transcription of viral RNPs. hnRNP M also interacts with influenza virus polymerase complex and is essential to maintain the efficient activity of both H1N1 and H5N1 influenza virus polymerases. Since Axin1 and Axin2 both promoted degradation of SPFQ and nonO/p54(nrb), our results here imply the relative less contribution of these two proteins to the antiviral property of Axin1. More importantly, Axin1 specifically induced degradation of hnRNP M. Recent data demonstrated that Axin1 is a central coordinator of c-Myc degradation through coupling to GSK3β signaling. Activation of GSK3β during influenza virus infection shown in our results (FIG. 8B) could also be implicated in Axin1-mediated degradation of these host factors.

TABLE 2

Physical interaction between Axin1 and IFIT1/2/3 during influenza virus infection:

|  | Bait | | | | | |
|---|---|---|---|---|---|---|
|  | GFP | | | Axin1 | | |
| PR/8 (dpi) | 0 | 8 | 24 | 0 | 8 | 24 |
| IFIT1 | 0 | 0 | 0 | 0 | 8.7 ± 1.4 | 6.3 ± 1.3 |
| IFIT2 | 0 | 0 | 0 | 0 | 7.3 ± 1.3 | 7.7 ± 0.7 |
| IFIT3 | 0 | 0 | 0 | 0 | 4.7 ± 0.3 | 12 ± 1.5 |
| IFIT5 | 0 | 0 | 0 | 0 | 0 | 0 |

HEK293 cells were transfected with OE-GFP or OE-Axin1 plasmids for 24 hours and then infected with H1N1 influenza A/PR/8/34 virus PR/8 (MOI=2) for 8 or 24 hours. Liquid chromatography and tandem mass spectrometry of protein complexes were isolated by immunoprecipication. Results are represented as number of peptides identified. Data from Table 2 are from three experiments and shown are means±s.e.m. RN-1 inhibits influenza virus replication.

To examine whether RN-1 has anti-influenza activity in vitro according to an embodiment, a human lung epithelial cell line, A549 cells, and primary mouse alveolar epithelial cells with RN-1 for 24 h were treated, then infected cells with influenza A/PR/8/34 virus at a MOI of 2 for 24 h, and determined virus titers in culture media. RN-1 attenuated influenza virus replication with an $EC_{50}$ of 419 nM and the maximum inhibition was over 99% in human A549 cells (FIG. 20A-D). At all the concentrations tested, RN-1 did not affect cell viability, indicating that RN-1 is not toxic to the cells. RN-1 also significantly inhibited virus replication in mouse lung primary epithelial cells (FIG. 1B). To identify potential mechanisms of action for RN-1, it was determined IFN and IFN-stimulated gene (ISG) expression. RN-1 increased the mRNA expression of IFNα1 (FIG. 1C) and the ISG, MX1 (FIG. 1D) in primary mouse alveolar epithelial cells during virus infection. However, RN-1 treatment of uninfected cells had no effects on the baseline IFN gene expression. These studies suggest that RN-1 represses influenza virus infection in cell culture, likely through stimulating host IFN response.

* * * * *

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art.

Applicant reserves the right to pursue at a later date any previously pending or other broader or narrower claims that capture any subject matter supported by the present disclosure, including subject matter found to be specifically disclaimed herein or by any prior prosecution.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is also to be understood that where the claims or specification use "a" or "an" to refer to an element, such reference is not be construed that there is only one of that element.

Where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Unless indicated otherwise, methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the range ending with that number (which may be a range having 1 or 0 as its lower limit or a range having no lower limit, depending upon the variable being defined). For example, "at most 4" means 4 or less than 4, and "at most 40%" means 40% or less than 40%.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

While this invention is susceptible of embodiments in many different forms, there is shown in the drawings, and is herein described in detail, some specific embodiments. It should be understood, however, that the present disclosure is to be considered an exemplification of the principles of the invention and is not intended to limit it to the specific embodiments or algorithms so described. Those of ordinary skill in the art will be able to make various changes and further modifications, apart from those shown or suggested herein, without departing from the spirit of the inventive concept, the scope of which is to be determined by the following claims.

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Still further, additional aspects of the instant invention may be found in one or more appendices attached hereto and/or filed herewith, the disclosures of which are incorporated herein by reference as if fully set out at this point.

Reviewers of the prosecution history of any parent, child or related case shall not reasonably infer that the applicants have made any disclaimers or disavowals of subject matter in the present case based on disclaimers or disavowals in such parent, child, or related case.

It should be noted that where reference is made herein to a method comprising two or more defined steps, the defined steps can be carried out in any order or simultaneously (except where context concludes that possibility), and the method can also include one or more other steps which are carried out before any of the defined steps, between two of the defined steps, or after all of the defined steps (except where context concludes that possibility).

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. A method of preventing, treating, or slowing the progression of a viral infection in a subject in need thereof, comprising
administering to said subject a therapeutically effective amount of a composition comprising
a stabilizer or enhancer of Axin1 activity; and
a pharmacologically acceptable carrier, where the viral infection is a respiratory viral infection.

2. The method of claim 1, wherein said stabilizer or enhancer of Axin1 activity is a tankyrase inhibitor.

3. The method of claim 2, wherein the tankyrase inhibitor is selected from the group consisting of a small molecule inhibitor, a macromolecule inhibitor and a recombinant peptide.

4. The method of claim 3, wherein said small molecule inhibitor is selected from the group consisting of:
XAV939 (3,5,7,8-Tetrahydro-2-[4-(trifluoromethyl)phenyl]-4H-thiopyrano [4,3-d]pyrimidin-4-one);
WIKI4 (2-[3-[[4-(4-Methoxyphenyl)-5-(4-pyridinyl)-4H-1,2,4-triazol-3-yl]thio]propyl]-1H-benz[de]isoquinoline-1,3(2H)-dione);
TNKSi49 (N-((1r,4r)-4-(4-cyanophenoxy)cyclohexyl)-3-((4-oxo-3,4-dihydroquinazolin-2-yl)thio)propanamide);
IWR-1 (4-(1,3,3a,4,7,7a-Hexahydro-1,3-dioxo-4,7-methano-2H-isoindo-2-yl)-N-8-quinolinyl-Benzamide);
G007-LK (4-(5-((E)-2-(4-(2-Chlorophenyl)-5-(5-(methylsulfonyl)pyridin-2-yl)-4H-1,-2,4-triazol-3-yl)ethenyl)-1,3,4-oxadiazol-2-yl)benzonitrile);
JW55 (N-(4-(((4-(4-methoxyphenyl)tetrahydro-2H-pyran-4-yl)methyl)carbamoyl)phenyl)furan-2-carboxamide);
JW74 (5-(((4-(4-methoxyphenyl)-5-(pyridin-4-yl)-4H-1,2,4-triazol-3-yl)thio)methyl)-3-(p-tolyl)-1,2,4-oxadiazole);
TNKS1/2 Inhibitor III (3-(4-Methoxyphenyl)-5-((4(4-methoxyphenyl)-5-methyl-4H-1,2,4-triazol-3-ylthio) methyl)-1,2,4-oxadiazole),
tankyrase Inhibitor (TNKS) 22(3-((4-oxo-3,4-dihydroquinazolin-2-yl)thio)-N-((1r,4r)-4-(5-phenyl-1,3,4-oxadiazol-2-yl)cyclohexyl)propanamide);
1,2,-Trizole

flavone (2-phenyl-4H-chromen-4-one)

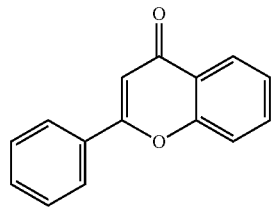 [SMILES: O=c1cc(-c2ccccc2)oc2ccccc12]

phenanthridin-6(5H)-one

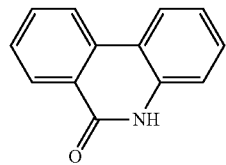

TIQ-A

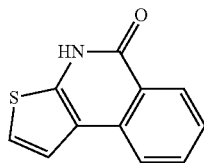

PJ34

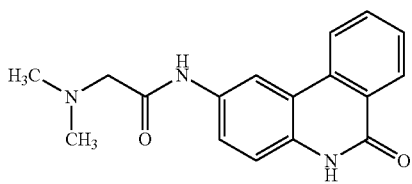 [SMILES: CN(C)CC(=O)Nc1ccc2[nH]c(=O)c3ccccc3c2c1]

1DY (N-(2-methoxyphenyl)-4-{[3-(4-oxo-3,4-dihydro-quinazolin-2-yl)propanoyl]amino}benzamide)

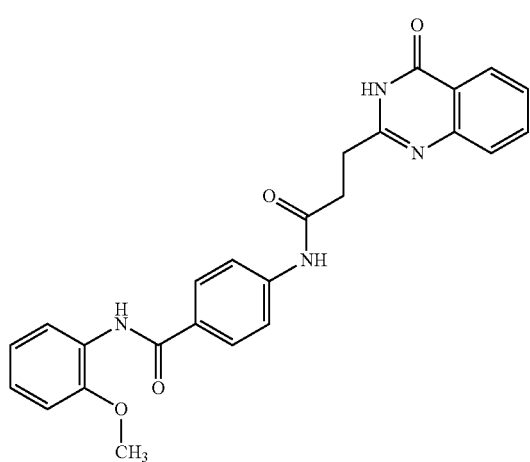 [SMILES: COc1ccccc1NC(=O)c1ccc(NC(=O)CCc2nc3ccccc3c(=O)[nH]2)cc1]

and
oxazolidinone

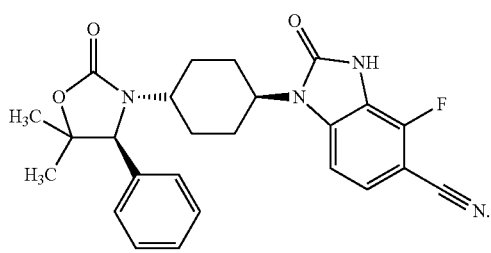

5. The method of claim 4, where the small molecule inhibitor is selected from the group consisting of XAV-939, a prodrug of XAV-939, an active metabolite of XAV-939, a salt of XAV-939, and combinations thereof.

6. The method of claim 1, where the respiratory viral infection is caused by a virus selected from the group consisting of: influenza virus, respiratory syncytial virus, rhinovirus, coronavirus, parainfluenza virus, adenovirus, enterovirus, measles virus, herpesvirus, reovirus, human metapneumovirus, SARS-coronaviruses, Epstein-Barr virus, cytomegalovirus, hantavirus, and bocavirus.

7. The method of claim 6, where the influenza virus is influenza A virus subtype H1N1.

8. The method of claim 1, wherein said one or more symptoms being selected from the group consisting of: fever, chills, cough, sore throat, runny nose, stuffy nose, muscle aches, body aches, headaches, fatigue, vomiting, diarrhea, weight loss, secondary pneumonia, secondary bronchitis, secondary sinus infection, and secondary ear infection.

9. The method of claim 3, wherein said small molecule inhibitor is selected from the group consisting of:
XAV939 (3,5,7,8-Tetrahydro-2-[4-(trifluoromethyl)phenyl]-4H-thiopyrano[4,3-d]pyrimidin-4-one);
WIKI4 (2-[3-[[4-(4-Methoxyphenyl)-5-(4-pyridinyl)-4H-1,2,4-triazol-3-yl]thio]propyl]-1H-benz[de]isoquinoline-1,3(2H)-dione);
TNKSi49 (N-((1r,4r)-4-(4-cyanophenoxy)cyclohexyl)-3-((4-oxo-3,4-dihydroquinazolin-2-yl)thio)propanamide);
IWR-1 (4-(1,3,3a,4,7,7a-Hexahydro-1,3-dioxo-4,7-methano-2H-isoindol-2-yl)-N-8-quinolinyl-Benzamide);
G007-LK (4-(5-((E)-2-(4-(2-Chlorophenyl)-5-(5-(methylsulfonyl)pyridin-2-yl)-4H-1,-2,4-triazol-3-yl)ethenyl)-1,3,4-oxadiazol-2-yl)benzonitrile);
JW55 (N-(4-(((4-(4-methoxyphenyl)tetrahydro-2H-pyran-4-yl)methyl)carbamoyl)phenyl)furan-2-carboxamide);
JW74 (5-(((4-(4-methoxyphenyl)-5-(pyridin-4-yl)-4H-1,2,4-triazol-3-yl)thio)methyl)-3-(p-tolyl)-1,2,4-oxadiazole);
TNKS1/2 Inhibitor III (3-(4-Methoxyphenyl)-5-((4-(4-methoxyphenyl)-5-methyl-4H-1,2,4-triazol-3-ylthio)methyl)-1,2,4-oxadiazole),
tankyrase Inhibitor (TNKS) 22 (3-((4-oxo-3,4-dihydroquinazolin-2-yl)thio)-N-((1r,4r)-4-(5-phenyl-1,3,4-oxadiazol-2-yl)cyclohexyl)propanamide);
1,2,-Trizole

flavone (2-phenyl-4H-chromen-4-one)

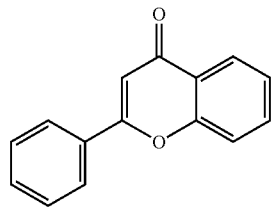 [SMILES: O=c1cc(-c2ccccc2)oc2ccccc12]

phenanthridin-6(5H)-one

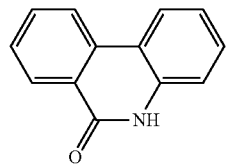 [SMILES: O=c1[nH]c2ccccc2c2ccccc12]

TIQ-A

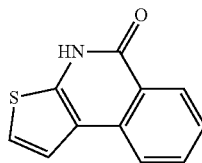

PJ34

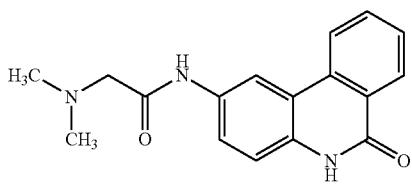 [SMILES: CN(C)CC(=O)Nc1ccc2[nH]c(=O)c3ccccc3c2c1]

1 DY (N-(2-methoxyphenyl)-4-{[3-(4-oxo-3,4-dihydro-quinazolin-2-yl)propanoyl]amino}benzamide)

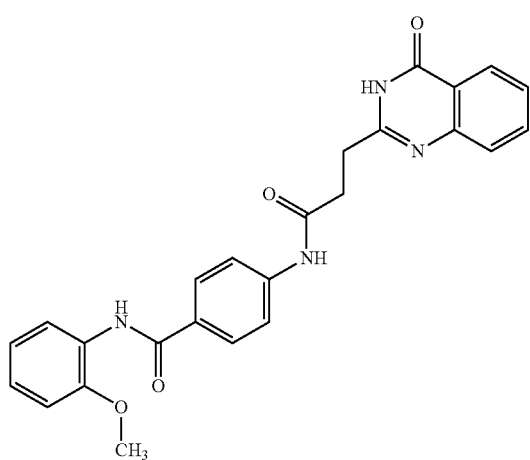 [SMILES: COc1ccccc1NC(=O)c1ccc(NC(=O)CCc2nc3ccccc3c(=O)[nH]2)cc1]

and
oxazolidinone

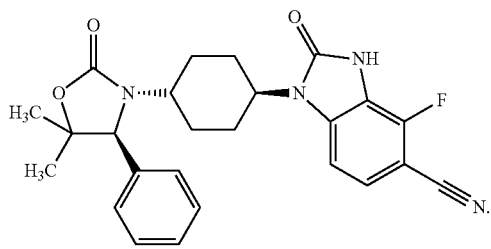

10. The method of claim 4, where the small molecule inhibitor is selected from the group consisting of XAV-939, a prodrug of XAV-939, an active metabolite of XAV-939, a salt of XAV-939, and combinations thereof.

11. A method of preventing, treating, or slowing the progression of a viral infection in a subject in need thereof, comprising administering to said subject a therapeutically effective amount of a composition comprising a stabilizer or enhancer of Axin1 activity; and
a pharmacologically acceptable carrier,
wherein
the viral infection is a respiratory viral infection;
the stabilizer or enhancer of Axin1 activity is a small molecule tankyrase inhibitor selected from the group consisting of:
XAV939 (3,5,7,8-Tetrahydro-2-[4-(trifluoromethyl)phenyl]-4H-thiopyrano[4,3-d]pyrimidin-4-one);
WIKI4 (2-[3-[[4-(4-Methoxyphenyl)-5-(4-pyridinyl)-4H-1,2,4-triazol-3-yl]thio]propyl]-1H-benz[de]isoquino-line-1,3(2H)-dione);
TNKSi49 (N-((1r,4r)-4-4-cyanophenoxy)cyclohexyl)-3-((4-oxo-3,4-dihydroquinazolin-2-yl)thio)propanamide);
IWR-1 (4-(1,3,3a,4,7,7a-Hexahydro-1,3-dioxo-4,7-methano-2H-isoindol-2-yl)-N-8-quinolinyl-Benzamide);
G007-LK (4-(5-((E)-2-(4-(2-Chlorophenyl)-5-(5-(methylsulfonyl)pyridin-2-yl)-4H-1,-2,4-triazol-3-yl)ethenyl)-1,3,4-oxadiazol-2-yl)benzonitrile);
JW55 (N-(4-(((4-(4-methoxyphenyl)tetrahydro-2H-pyran-4-yl)methyl)carbamoyl)phenyl)furan-2-carboxamide);
JW74 (5-(((4-(4-methoxyphenyl)-5-(pyridin-4-yl)-4H-1,2,4-triazol-3-yl)thio)methyl)-3-(p-tolyl)-1,2,4-oxadiazole);
TNKS1/2 Inhibitor III (3-(4-Methoxyphenyl)-5-((4-(4-methoxyphenyl)-5-methyl-4H-1,2,4-triazol-3-ylthio)methyl)-1,2,4-oxadiazole),
tankyrase Inhibitor (TNKS) 22(3-((4-oxo-3,4-dihydroquinazolin-2-yl)thio)-N-((1r,4r)-4-(5-phenyl-1,3,4-oxadiazol-2-yl)cyclohexyl)propanamide);
1,2,-Trizole

flavone (2-phenyl-4H-chromen-4-one)

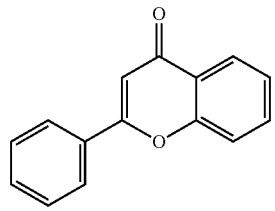 [SMILES: O=c1cc(-c2ccccc2)oc2ccccc12]

phenanthridin-6(5H)-one

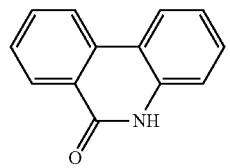 [SMILES: O=c1[nH]c2ccccc2c2ccccc12]

TIQ-A

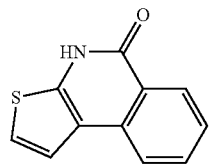 [SMILES: O=c1[nH]c2sccc2c2ccccc12]

PJ34

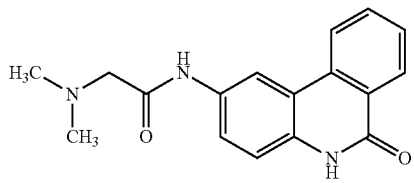 [SMILES: CN(C)CC(=O)Nc1ccc2[nH]c(=O)c3ccccc3c2c1]

1DY (N-(2-methoxyphenyl)-4-{[3-(4-oxo-3,4-dihydro-quinazolin-2-yl)propanoyl]amino}benzamide)

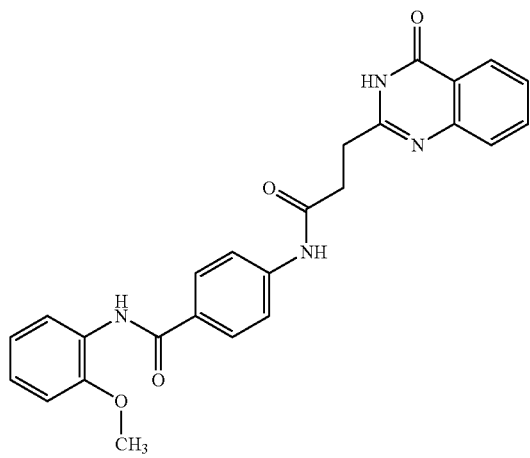 [SMILES: COc1ccccc1NC(=O)c1ccc(NC(=O)CCc2nc3ccccc3c(=O)[nH]2)cc1]

and oxazolidinone

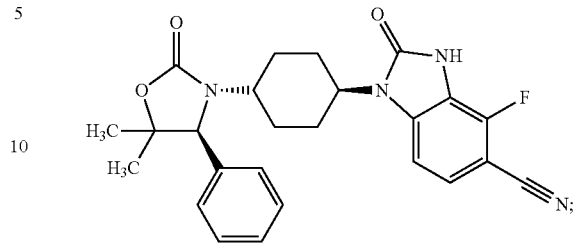

and the subject suffers from a respiratory viral infection symptom selected from the group consisting of: fever, chills, cough, sore throat, runny nose, stuffy nose, muscle aches, body aches, headaches, fatigue, vomiting, diarrhea, weight loss, secondary pneumonia, secondary bronchitis, secondary sinus infection, and secondary ear infection.

12. The method of claim 1, wherein the respiratory viral infection is an acute respiratory infection.

13. The method of claim 1, wherein the respiratory viral infection includes an infection of lung and/or alveolar cells of the subject.

14. The method of claim 1, wherein the stabilizer or enhancer of Axin1 activity is administered by absorption through mucocutaneous cell linings.

15. The method of claim 1, wherein the stabilizer or enhancer of Axin1 activity is administered by inhalation.

16. The method of claim 1, wherein the stabilizer or enhancer of Axin1 activity is administered orally.

17. The method of claim 1, wherein the stabilizer or enhancer of Axin1 activity is administered intranasally.

18. The method of claim 1, wherein the stabilizer or enhancer of Axin1 activity is administered as a mist, as a spray, as eye drops, as a pill, as a capsule or as a liquid.

* * * * *